United States Patent [19]
Cook et al.

[11] Patent Number: 5,798,360
[45] Date of Patent: Aug. 25, 1998

[54] N-(AMINOALKYL)- AND/OR N-(AMIDOALKYL)- DINITROGEN HETEROCYCLIC COMPOSITIONS

[75] Inventors: Phillip Dan Cook, Vista; Andrew M. Kawasaki, Oceanside; Pei Pei Kung, Leucadia, all of Calif.

[73] Assignee: ISIS Pharmaceuticals, Inc., Carlsbad, Calif.

[21] Appl. No.: 688,993

[22] Filed: Aug. 1, 1996

[51] Int. Cl.$^6$ .................................................. A61K 31/505
[52] U.S. Cl. ...................... 514/255; 514/385; 514/210; 514/218
[58] Field of Search ............................. 514/255, 385, 514/210, 218

[56] References Cited

U.S. PATENT DOCUMENTS

| | | | |
|---|---|---|---|
| 4,988,814 | 1/1991 | Abou-Gharbia et al. | 544/295 |
| 5,143,854 | 9/1992 | Pirrung et al. | 436/518 |
| 5,449,754 | 9/1995 | Nishioka | 530/334 |
| 5,472,672 | 12/1995 | Brennan | 422/131 |
| 5,489,678 | 2/1996 | Fodor et al. | 536/22.1 |

FOREIGN PATENT DOCUMENTS

| | | |
|---|---|---|
| WO 93/04204 | 3/1993 | WIPO. |
| WO 93/20242 | 10/1993 | WIPO. |
| WO 93/22678 | 11/1993 | WIPO. |
| WO 94/28028 | 12/1994 | WIPO. |

OTHER PUBLICATIONS

PCT International Search Report dated Jan. 14, 1998, 2 pages.

Bourrain, S. et al., "Isoxazole and pyrazole derivatives as dopamine receptor subtype ligands, and their preparation, compositions, and use", Jun. 1, 1995, Database CAPLUS on STN, Document No. 123:169618 (Abstract Only).

Debernardis, J.F. et al., "Preparation of 1-aryl-3-piperazineopropanones for treatment of Alzheimer's disease", May 30, 1996, Database CAPLUS on STN, Document No. 125:142771 (Abstract Only).

Ferrini, P.G. et al., "Preparation of substituted benzoyl-and benzylphenethylpiperazines as analgesics", Dec. 23, 1987, Database CAPLUS on STN, Document No. 108:112502 (Abstract Only).

Krishnan, R. et al., "Antibacterial activity of 6,8-disubstituted-quinolone-3-carboxylic acids", J. Pharm. Sci., 1986, 75(12), 1185–1187, Document No. 106:156251 (Abstract Only).

Meyer, W.E. et al, "5-(1-Piperazinyl)-1H-1,2,4-triazol-3-amines as antihypertensive agents", J. Med. Chem., 1989, 32(3), 593–597, Document No. 110:205054 (Abstract Only).

Modak, S.M. et al., "Pharmaceutical compositions for inactivating irritants in fluids containing antimicrobial agents", Oct. 5, 1995, Database CAPLUS on STN, Document No. 124:66587 (Abstract Only).

Protiva, M. et al., "Part IV. 1-Aryl-and 1-(arylmethyl)-4-guanylpiperazines and other heterocyclic and alicyclic guanidine derivatives", Collect. Czech. Chem. Commun., 1975, 40(12), 3904–3923, Document No. 84:180165 (Abstract Only).

Tamada, S. et al., "Preparation of 4-oxoquinolines as cardiotonics, vasodilators, and inflammation inhibitors", Mar. 8, 1989, Database CAPLUS on STN, Document No. 111:194610 (Abstract Only).

Tone, H. et al., "Preparation of pyrazine oxides as drugs", Nov. 4, 1992, Database CAPLUS on STN, Document No. 118:124562 (Abstract Only).

Yaso, M. et al., "Preparation of 1-(substituted alkyl)-2(1H)-pyrazinones as cardiovascular agents", Sep. 2, 1987, Database CAPLUS on STN, Document No. 108:167501 (Abstract Only).

Achari et al., "Facing up to Membranes: Structure/Function Relationships in Phospholipases", Cold Spring Harbor Symp. Quant. Biol., 1987, 52, 441–452.

Bomalaski et al., "Human Extracellular Recombinant Phospholipase $A_2$ Induces an Inflammatory Response in Rabbit Joints", J. Immunol., 1991, 146(11), 3904–3910.

Burack et al., "Role of Lateral Phase Separation in the Modulation of Phospholipase $A_2$ Activity", Biochemistry, 1993, 32, 583–589.

Campbell et al., "Inhibition of Phospholipase $A_2$; a Molecular Recognition Study", J. Chem. Soc. Chem. Commun., 1988, 1560–1562.

Cho et al., "The Chemical Basis for Interfacial Activation of Monomeric Phospholipases $A_2$", J. Biol. Chem., 1988, 263(23), 11237–11241.

Davidson et al., "Inhibition of Phospholipase $A_2$ by Lipocortins and Calpactins", J. Biol. Chem., 1987, 262(4), 1698–1705.

Davidson et al., "1-Stearyl,2-Stearoylaminodeoxy Phosphatidylcholine, A Potent Reversible Inhibitor of Phospholipase $A_2$", Biochem. Biophys. Res. Commun., 1986, 137(2), 587–592.

Dennis, E.A., "Phospholipases", The Enzymes, Boyer, P.D. (ed.), Academic Press, New York, 1983, vol. 16, 307–353.

Essien, H., "Synthesis of Diethylenetriaminepentaacetic Acid Conjugated Inulin and Utility for Cellular Uptake of Liposomes", J. Med. Chem., 1988, 31, 898–901.

(List continued on next page.)

*Primary Examiner*—Jane Fan
*Attorney, Agent, or Firm*—Woodcock Washburn Kurtz Mackiewicz & Norris LLP

[57] ABSTRACT

Compositions are provided comprising novel di-nitrogen heterocycle compounds containing N-(aminoalkyl) and/or N-(amidoalkyl) groups. An additional situs of functionality is also provided. The compounds and compositions of the invention are useful as antibacterial and other pharmaceutical agents and as intermediates for preparation of other pharmaceutical agents. In addition, compounds of the present invention are useful as research reagents including employment as species for effecting combinatorial synthesis.

24 Claims, No Drawings

OTHER PUBLICATIONS

Franson et al., "Phospholipid metabolism by phagocytic cells. Phospholipases $A_2$ associated with rabbit polymorphonuclear leukocyte granules", *J. Lipid Res.*, 1974, 15, 380–388.

Glaser et al., "Phospholipase $A_2$ enzymes: regulation and inhibition", *TiPs Reviews*, 1993, 14, 92–98.

Grainger et al., "An enzyme caught in action: direct imaging of hydrolytic function and domain formation of phospholipase $A_2$ in phosphatidylcholine monolayers", *FEBS Lett.*, 1989, 252(1,2), 73–82.

Lombardo et al., "Cobra Venom Phospholipase $A_2$ Inhibition by Manoalide", *J. Biol. Chem.*, 1985, 260(12), 7234–7240.

Marki et al., "Differential inhibition of human secretory and cytosolic phospholipase $A_2$", *Agents Actions*, 1993, 38, 202–211.

Miyake et al., "The Novel Natural Product YM–26567–1 [(+)-trans–4-(3–dodecanoyl–2,4,6–trihydroxyphenyl)–7–hydroxy–2-(4–hydroxyphenyl)chroman]: A Competitive Inhibitor of Group II Phospholipase $A_2$", *J. Pharmacol. Exp. Ther.*, 1992, 263(3), 1302–1307.

Noel et al., "Phospholipase $A_2$ Engineering. 3. Replacement of Lysine–56 by Neutral Residues Improves Catalytic Potency Significantly, Alters Substrate Specificity, and Clarifies the Mechanism of Interfacial Recognition", *J. Am. Chem. Soc.*, 1990, 112, 3704–3706.

Oinuma et al., "Synthesis and Biological Evaluation of Substituted Benzenesulfonamides as Novel Potent Membrane–Bound Phospholipase $A_2$ Inhibitors", *J. Med. Chem.*, 1991, 34, 2260–2267.

Pruzanski et al., "Enzymatic Activity and Immunoreactivity of Extracellular Phospholipase $A_2$ in Inflammatory Synovial Fluids", *Inflammation*, 1992, 16(5), 451–457.

Sampson, B.A. et al., "Identification and Characterization of a New Gene of *Escherichia coli* K–12 Involved in Outer Membrane Permeability", *Genetics*, 1989, 122, 491–501.

Scott et al., "Interfacial Catalysis: The Mechanism of Phospholipase $A_2$", *Science*, 1990, 250, 1541–1546.

Pon, R.T., "Solid Phase Supports in Oligonucleotide Synthesis", Protocols for Oligonucleotides and Analogs: Synthesis and Properties, Agrawal, S., ed., Humana Press, 1993, 20, 465–496.

Tanaka et al., "A Novel Type of Phospholipase $A_2$ Inhibitor, Thielocin A1β, and Mechanism of Action", *J. Antibiotics*, 1992, 45(7), 1071–1078.

Vishwanath et al., "Edema–Inducing Activity of Phospholipase $A_2$ Purified from Human Synovial Fluid and Inhibition by Aristolochic Acid", *Inflammation*, 1988, 12(6), 549–561.

Vloon, W.J. et al., "Synthesis and Biological Properties of Side–Chain–Modified Bleomycins", *J. Med. Chem.*, 1987, 30, 20–24.

Washburn et al., "Suicide–inhibitory Bifunctionally Linked Substrates (SIBLINKS) as Phospholipase $A_2$ Inhibitors", *J. Biol. Chem.*, 1991, 266(8), 5042–5048.

Wery et al., "Structure of recombinant human rheumatoid arthritic synovial fluid phospholipase $A_2$ at 2.2 Å resolution", *Nature*, 1991, 352, 79–82.

Yang et al., "Studies on the status of lysine residues in phospholipase $A_2$ from Naja naja atra (Taiwan cobra) snake venom", *Biochem. J.*, 1989, 262, 855–860.

Yuan et al., "Synthesis and Evaluation of Phospholipid Analogues as inhibitors of Cobra Venom Phospholipase $A_2$", *J. Am. Chem. Soc.*, 1987, 109, 8071–8081.

Yuan, J. et al., "Synthesis of Some 2–Substituted Aminobenzothiazoles", *Acta Scientiarum Naturalium*, (Beijing Daxue Zuebao, Ziran Kexueban), 1988, 24(4), 504–506 (English Abstract).

Maffrand et al., CA 87:85048, 1977.

N-(AMINOALKYL)- AND/OR N-(AMIDOALKYL)- DINITROGEN HETEROCYCLIC COMPOSITIONS

FIELD OF THE INVENTION

This invention relates to combinations of di-nitrogen heterocycles and their uses, inter alia in pharmaceuticals.

BACKGROUND OF THE INVENTION

From the discovery of penicillin by Fleming in 1940's there has been a constant search for new antibiotics, which search continues to this day. Although many antibiotics have been discovered, there is an on-going need for the discovery of new antibiotic compounds because of the emergence of drug resistant strains of bacteria. Thus, research on bacterial infection is a perpetual cycle of development of new antibiotics. When penicillin was first discovered, its broad-spectrum antibiotic activity was hailed as the "magic bullet" in fighting many bacterial infections. However, over the years, many strains of bacteria have developed a resistance to penicillin and other currently available antibiotic drugs. No antibiotic drug is effective against all bacterial infections. Many antibiotic drugs available today have narrow-spectrum of activity, that is, they are effective against only few specific types of bacterial infections. Thus, for example, the majority of current antibiotic drugs are ineffective against syphilis and tuberculosis. In addition, some strains of syphilis, tuberculosis and other bacteria have developed resistance to currently available antibiotic drugs, which were effective drugs in the past.

Most bacteria which are resistant to a given drug also exhibit similar resistance to chemically similar drugs. Currently, many antibiotics are based on the β-lactam chemical core structure of penicillin. Although other chemically diverse antibiotics, such as vancomycin, are currently available, it is only a matter of time before the emergence of bacterial strains which will be resistant to all currently available antibiotic drugs. Thus, to prevent a future worldwide epidemic of drug resistant bacterial infections, there is a never ending need for a development of antibiotic drugs with novel chemical structures. This invention addresses this goal among others.

It is, accordingly, an object of this invention to provide novel di-nitrogen heterocycle compounds and combinations of such compounds for use in the preparation of antibiotics and other pharmaceuticals.

A further object of the invention is to provide combinations of such compounds in a form such that resulting compositions have structurally and chemically diverse properties for use as research reagents and otherwise.

Yet another object is to provide products produced by processes herein disclosed for the preparation of pharmaceuticals and other useful chemical species.

A further object is to provide methods for the identification of useful drugs and reagents.

These and other objects will become apparent to persons of ordinary skill in the art from a review of the present specification and appended claims.

SUMMARY OF THE INVENTION

In one aspect, the present invention is directed to compounds having a di-nitrogen-containing heterocyclic portion to which pluralities of substituents are appended. In accordance with preferred embodiments, compositions are prepared comprising a plurality of such compounds, preferably more than three and even more preferably, more than six, such that such compositions can be seen to be mixtures of species having a di-nitrogen heterocyclic framework. It is preferred that the substituents appended to the framework, preferably the di-nitrogen heterocyclic frameworks as discussed hereinafter, be varied in terms of size, hydrophobicity, charge, chemistry, orientation, and subsequent reactivity. The resulting compositions are useful per se, as, for example, antibiotics, reagents for use in scientific research, and otherwise. Certain preferred compositions, comprising mixtures of such compounds, have been shown to have antibiotic activity and otherwise to be useful.

This invention is also directed to constituent portions of novel compounds, which components can be combined to form compositions having utility per se as well as in the preparation and identification of more complex pharmaceutical and other compositions.

In accordance with preferred embodiments of the present invention, compositions are provided comprising the reaction products of di-nitrogen heterocycles with chemically diverse substituents. Compounds of one such type have Formula I:

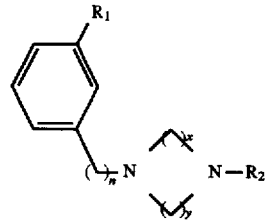

wherein
each of n, x and y is 1, 2 or 3;
$R_1$ is halogen, cyano, $C_1-C_6$ alkyl, perhalo $C_1-C_3$ alkyl, nitro, nitroso or carboxylate, and
$R_2$ is hydrogen, $C_1-C_6$ alkyl, $C_6-C_{15}$ aryl, $C_7-C_{20}$ alkaryl, $C_4-C_{15}$ heterocycle or a moiety of the formula —$(CH_2)_m$—$R_3$—$R_4$ where
m is 0 or 1;
$R_3$ is —$CH_2$—, —$C(=O)$— or —$C(=S)$—; and
$R_4$ is —O—$R_5$, —$N(R_5)(R_6)$, —$N(R_5)$—O—$R_6$, $C_1-C_6$ alkyl, $C_6-C_{15}$ aryl or $C_4-C_{15}$ heterocycle where $R_5$ and $R_6$ are independently hydrogen, $C_1-C_6$ alkyl, $C_6-C_{15}$ aryl, $C_3-C_{12}$ cycloalkyl, $C_4-C_{15}$ heterocycle or $C_7-C_{20}$ alkaryl.

It is preferred that such compositions comprise a plurality of compounds having Formula I (or other formulas set forth herein). Such compositions have been shown to have antibiotic activity and, hence, to be useful in the formulation of pharmaceuticals and otherwise.

In a preferred embodiment of the present invention, the compounds in accordance with Formula I are such that n is 1 or 2, and each of x and y is 2 or 3. More preferably n is 1, and x and y are 2.

In another preferred embodiment of the invention, $R_1$ is halogen, cyano, $C_1-C_6$ alkyl, perhalo $C_1-C_3$ alkyl, nitro, or carboxylate. Exemplary $C_1-C_6$ alkyls include, methyl, ethyl, propyl, butyl, t-butyl, pentyl and hexyl. Exemplary perhalo $C_1-C_3$ alkyls include, trifluoromethyl, trichloromethyl, triiodomethyl, pentafluoroethyl, pentachloroethyl, and heptafluoropropyl. Exemplary carboxylates include methyl carboxylate, ethyl carboxylate, t-butyl carboxylate, and sodium carboxylate. More preferably, $R_1$ is fluorine, cyano, methyl, trifluoromethyl or methyl carboxylate.

In yet another preferred embodiment of the invention, $R_2$ is hydrogen, $C_6-C_{15}$ aryl, $C_7-C_{20}$ alkaryl, $C_4-C_{15}$ heterocycle or a moiety of the formula —$(CH_2)_m$—$R_3$—$R_4$. Heterocycles are ring systems which contain one or more of heteroatoms, such as O, N or S. A heterocycle may be aromatic or contain one or more non-aromatic unsaturated bonds, i.e., π-bonds. Exemplary $C_4$-$C_{15}$ heterocycles include pyran, pyrrolidone, benzothiazole, pyridine, benzoxzole, piperidine, piperazine, furan, thiofuran, pyrimidine and carbazole. Exemplary $C_6$-$C_{15}$ aryls include phenyl, aminophenyl, halophenyl, methoxyphenyl, hydroxyphenyl, toluyl, trifluoromethylphenyl, xylyl, ethylphenyl, propylphenyl, naphthyl, bromonaphthyl, chloronaphthyl, methylnaphthyl, hydroxynaphtyl, anthracyl, bromoanthracyl, and chloroanthracyl. Halophenyls are phenyl groups with one or more halogens substituted on the phenyl ring. Exemplary halophenyls include chlorophenyl, bromophenyl, chlorophenyl, fluorophenyl, dichlorophenyl, chlorofluorophenyl and dibromophenyl. A preferred halophenyl is o-chlorophenyl. Exemplary $C_7$-$C_{20}$ alkaryl include benzyl, methoxybenzyl, bromobenzyl, fluorobenzyl, naphthylmethyl, methoxyphenylmethyl, acetoxyphenylmethyl, 2-phenylethyl, 2-naphthylethyl, 3-phenylpropyl and 2-phenylpropyl.

More preferably, $R_2$ is hydrogen, phenyl, halophenyl, m-trifluoromethylphenyl, benzyl, m-methylbenzyl, m-nitrobenzyl, m-fluorobenzyl, m-cyanobenzyl, m-trifluoromethylbenzyl, m-methylcarboxylbenzyl, 6-trifluoromethyl-2-pyridyl or a moiety of the formula —$(CH_2)_m$—$R_3$—$R_4$.

$R_3$ is —$CH_2$—, —$C(=O)$— or —$C(=S)$—. Preferably, $R_3$ is —$CH_2$— or —$C(=O)$—, and m is 0 or 1.

$R_4$ is —O—$R_5$, —$N(R_5)(R_6)$, —$N(R_5)$—O—$R_6$, $C_1$-$C_6$ alkyl, $C_6$-$C_{15}$ aryl or $C_4$-$C_{15}$ heterocycle. Preferably, $R_4$ is —O—$R_5$, —$N(R_5)(R_6)$, —$N(R_5)$—O—$R_6$, $C_6$-$C_{15}$ aryl or $C_4$-$C_{15}$ heterocycle. Preferred $C_6$-$C_{15}$ aryl groups for $R_4$ are phenyl, m-methylphenyl, m-nitrophenyl, m-fluorophenyl, m-cyanophenyl, m-trifluoromethylphenyl or m-methylcarboxylphenyl. A preferred $C_4$-$C_{15}$ heterocycle for $R_4$ is 3-(2',4'-dichlorophenyl)-5-isoxazolyl.

$R_5$ and $R_6$ are independently hydrogen, $C_1$-$C_6$ alkyl, $C_6$-$C_{15}$ aryl, $C_3$-$C_{12}$ cycloalkyl, $C_4$-$C_{15}$ heterocycle or $C_7$-$C_{20}$ alkaryl. Preferably, $R_5$ is hydrogen, $C_1$-$C_6$ alkyl or $C_7$-$C_{20}$ alkaryl. Preferred $C_1$-$C_6$ alkyl groups for $R_5$ are methyl and t-butyl. Preferred $C_7$-$C_{20}$ alkaryl groups for $R_5$ are benzyl, m-methylbenzyl, m-nitrobenzyl, m-fluorobenzyl, m-cyanobenzyl, m-trifluoromethylbenzyl and m-methylcarboxylbenzyl.

Preferably $R_6$ is hydrogen, $C_1$-$C_6$ alkyl, $C_3$-$C_{12}$ cycloalkyl, $C_4$-$C_{15}$ heterocycle or $C_7$-$C_{20}$ alkaryl. Cycloalkyl groups can be monocyclic, bicyclic, bridged cyclic or polycyclic. Cycloalkyl groups also can be substituted. Exemplary cycloalkyl groups include cyclopropane, cyclobutane, cyclopentane, cyclohexane, cycloheptane, cyclooctane, cyclononane, cyclodecane, cycloundecane, cyclododecane, adamantane, norcamphor, [3.3.0] bicyclooctane and norborneol. A preferred $C_3$-$C_{12}$ cycloalkyl for $R_6$ is cycloheptyl. A preferred $C_1$-$C_6$ alkyl for $R_6$ is methyl. A preferred $C_4$-$C_{15}$ heterocycle for $R_6$ is 2-benzothiazolyl, and a preferred $C_7$-$C_{20}$ alkaryl for $R_6$ is benzyl.

In accordance with other embodiments of the present invention, compositions are provided comprising compounds having Formula II or III:

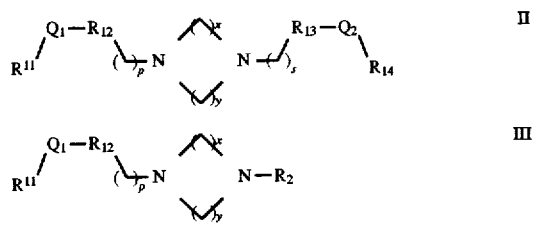

wherein
p and s are independently 0, 1 or 2;
x and y are independently 1, 2 or 3;
$Q_1$ and $Q_2$ are independently —$N(R_{15})$—, —O— or —S—;
each $R_2$ is hydrogen, $C_1$-$C_6$ alkyl, $C_6$-$C_{15}$ aryl, $C_7$-$C_{20}$ alkaryl, $C_4$-$C_{15}$ heterocycle or a moiety of the formula —$(CH_2)_m$—$R_3$—$R_4$ where:
  each m is 0 or 1;
  each $R_3$ is —$CH_2$—, —$C(=O)$— or —$C(=S)$—; and
  each $R_4$ is —O—$R_5$, $C_1$-$C_6$ alkyl, $C_6$-$C_{15}$ aryl or $C_4$-$C_{15}$ heterocycle,
  where each $R_5$ and $R_6$ are independently hydrogen, $C_1$-$C_6$ alkyl, $C_6$-$C_{15}$ aryl, $C_3$-$C_{12}$ cycloalkyl, $C_4$-$C_{15}$ heterocycle or $C_7$-$C_{20}$ alkaryl;
$R_{11}$ and $R_{14}$ are independently hydrogen, $C_1$-$C_6$ alkyl, $C_7$-$C_{20}$ alkaryl, $C_6$-$C_{20}$ aryl, $C_4$-$C_{15}$ heterocycle or $C_3$-$C_{20}$ cycloalkyl;
$R_{12}$ and $R_{13}$ are independently —$CH_2$—, —$C(=S)$— or —$C(=O)$—; and
each $R_{15}$ is independently hydrogen or $C_1$-$C_6$ alkyl.

These compounds may be seen to relate to N-(aminoalkyl)- and/or N-(amidoalkyl)-dinitroheterocycles. In certain preferred embodiments of the present invention, p and s are independently 0 or 1, and x and y are independently 2 or 3. More preferably, p and s are 1, and x and y are 2. In another preferred embodiment of the present invention, $Q_1$ and $Q_2$ are —$N(R_{15})$—.

It is also preferred in some embodiments of the present invention that $R_{11}$ and $R_{14}$ be independently $C_1$-$C_6$ alkyl, $C_7$-$C_{20}$ alkaryl, $C_6$-$C_{20}$ aryl, $C_4$-$C_{15}$ heterocycle or $C_3$-$C_{20}$ cycloalkyl. More preferably, $R_{11}$ and $R_{14}$ are independently $C_7$-$C_{20}$ alkaryl, $C_6$-$C_{20}$ aryl, $C_4$-$C_{15}$ heterocycle or $C_3$-$C_{20}$ cycloalkyl. Still more preferably, $R_{11}$ and $R_{14}$ are independently $C_6$-$C_{20}$ aryl, $C_4$-$C_{15}$ heterocycle or $C_3$-$C_{20}$ cycloalkyl. Even more preferably, $R_{11}$ and $R_{14}$ are independently selected from the group consisting of substituted or unsubstituted phenyl, furanyl, pyridyl, benzothiazolyl, thiofuranyl, naphthyl, pyrimidyl, cyclopropyl, cyclobutyl, cyclopentyl, cyclohexyl, cycloheptyl, cyclooctyl, cyclononyl, cyclodecyl and cyclododecyl. Still even more preferably, $R_{11}$ and $R_{14}$ are independently 2-benzothiazolyl, cycloheptyl or p-methoxyphenyl.

In other preferred embodiments, $R_{12}$ and $R_{13}$ are independently —$C(=O)$— or —$CH_2$—. In still other preferred embodiments, $R_{15}$ is hydrogen, such that $Q_1$ and $Q_2$ are —NH—.

Compounds which form the composition of the invention can be synthesized in accordance with reaction schemes employing standard, individual reactions. Exemplary reaction schemes are described in detail in the accompanying examples. However, persons of ordinary skill in the art should have no difficulty in determining routes to the synthesis of particular individual species or mixtures contemplated hereby.

In accordance with preferred embodiments of this invention, compositions are provided which comprise mixtures of compounds of the invention. Surprisingly, it has been found that such compositions have antibacterial activity, in some cases against both Gram negative and Gram positive bacteria.

Compositions comprising compounds disclosed herein are useful as antibiotics as well as in other therapeutic areas including treatment of fungal infections, viral infections, various type of neoplastic disease, cardiovascular diseases, central nervous system disorders, inflammation and immune disorders. Compositions of the present invention can inhibit both Gram positive bacteria, exemplified by *Escherichia Coli* (*E. Coli*), and Gram negative bacteria, such as *Streptococcus Pyogenes* (*S. Pyogenes*). Accordingly, the present invention provides therapeutic regimes against bacterial infection employing compositions set forth herein. In addition to antibiotic activities, compounds of the present invention are useful in other pharmaceutical areas and as intermediates for preparation and discovery of pharmaceutically active agents. The nitrogen heterocycles of the invention are likely to be useful in a number of therapeutic arenas, including muscle relaxants (as, for example, pipercurium bromide), anthelminthic drugs (as, for example, piperazine and its analogues), antineoplastic agents (as, for example, piposulfan), biological buffers (as, for example, piperazine derivatives such as piperazinediethanesulfonic acid), antiulcerative agents (as, for example, pirenzepine), antihypertensive agents (as, for example, prazosin), and antiinflammatory agents (as, for example, protacine (proglumetacin)). Compounds of the present invention can also be used in or as an intermediate for preparing or discovering drugs useful in the treatment of neoplastic diseases, immune disorders, cardiovascular diseases, central nervous system disorders and inflammation, among others.

For pharmaceutical use, it is well within the skill of those skilled in the art to ascertain routes of drug administration and dosage levels for particular compositions of matter of this invention in view of the objects thereby to be attained. Thus, the dosage forms of the present invention can be administered orally, rectally, parenterally, or transdermally, alone or in combination with other psychostimulants, antidepressants, and the like to a patient in need of treatment. Oral dosage forms include tablets, capsules, dragees, and other conventional, pharmaceutical forms. Isotonic saline solutions, conveniently containing about 1–200 milligrams of drug per milliliter can be used for parenteral administration which includes intramuscular, intrathecal, intravenous and intra-arterial routes. Rectal administration can conveniently be effected through the use of suppositories such as can easily be formulated from conventional carriers such as cocoa butter. Transdermal administration can be effected through the use of transdermal patch delivery systems and the like. The preferred routes of administration are oral and parenteral.

The dosage employed should be carefully titrated to the patient, considering age, weight, severity of the condition, and clinical-profile. The actual decision as to dosage will depend upon the exact drug being employed and will be made by the attending physician as a matter of routine. Such physician can, however, determine an appropriate regime employing well-known medical considerations. Unit dosage forms are selected as a matter of routine depending upon the selected route of administration. For oral administration, formulation into tablets using tabletting excipients are conveniently employed, although capsular and other oral forms are also useful.

The terms "pharmaceutical", "pharmaceutically active" and "pharmaceutically useful" are used interchangeably herein and refer to ability of the compounds of the present invention to provide some therapeutic or physiological beneficial, effect. As used herein, the terms include any physiologically or pharmacologically activity that produces a localized or systemic effect or effects in animals, including warm blooded mammals such as humans. Pharmaceutically active agents may act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autocoid systems, the alimentary and excretory systems, the histamine system and central nervous systems as well as other biological systems. Thus, the compounds of the present invention may be used as sedatives, psychic energizers, tranquilizers, anticonvulsants, muscle relaxants, antiparkinson agents, analgesics, antiinflammatories, local anesthetics, muscle contractants, antibiotic, antiviral, antiretroviral, antimalarials, diuretics, lipid regulating agents, antiandrogenic agents, antiparasitics, neoplastics, antineoplastics and chemotherapy agents. The compounds of the present invention could further be used to treat cardiovascular diseases, central nervous system diseases, cancer, metabolic disorders, infections and dermatological diseases as well as other biological disorders and infections.

Among the uses of the compositions and compounds of the present invention are uses in scientific research as research reagents. In accordance with the present invention, it is now possible to prepare pluralities of compounds in accordance with the invention to form a composition of matter in the nature of a "library" of compounds for research. Such libraries are known to be useful, per se and are important in the discovery, inter alia, of new drugs. In view of the chemical diversity present in such compounds, e.g. the large number of functional groups and functionalizable sites, a very large number of different compounds can be prepared. Moreover, such compounds can be prepared differentially, that is, in such a fashion that a population of known species can be prepared reliably, ensuring that all potential members of a family of chemical species are, in fact, synthesized.

In view of the foregoing, persons of ordinary skill in the art will know how to synthesize such libraries, comprising chemical compositions within the scope and spirit of this invention, and to assay the libraries against etiological agents or in tests or assays, in order to identify compounds having antibacterial, antifungal, antiviral, antineoplastic or other desired pharmaceutical, biological, or chemical activity.

For example, compounds of the present invention may be used in any of the many combinatorial drug identification methodologies known to persons skilled in the art of subsequently developed. Exemplary uses of this type are those described in Fodor et al., U.S. Pat. No. 5,489,678; Pirrung et al. U.S. Pat. No. 5,143,854; Lerner et al., PCT patent application WO 93/20242; Lebl et al. PCT patent application WO 94/28028; Hollis et al. PCT patent application WO 93/22678; Brennan U.S. Pat. No. 5,472,672, Nishioka U.S. Pat. No. 5,449,754 and Ecker et al., PCT patent application WO 93/04204.

As will be readily apparent to persons of skill in the art from a review of the present specification, useful compositions can be obtained by preparing mixtures of compounds formed from the constituent moieties forming the present compounds. Thus, compounds formed by reacting reactive appendage compounds such as meta benzylic compounds, alpha-amide compounds or other compounds having a reactive group thereupon, with one or a family of scaffold molecules having a plurality of reactive functionalities thereupon have great utility as pharmaceuticals. It is preferred that the scaffold molecules have at least one reactive functionality which can react with the reactive functionality on the appendage molecules, together with at least one additional reactive moiety for reaction with other appendages or functional groups. For example, the scaffold molecules conveniently have nucleophilic functionalities while the appendage molecules are comprise one or more leaving groups. The reverse can also be true, however, such that the scaffold molecules have electrophilic centers and leaving groups while the appendages are nucleophilic. Other reactions may also be employed in this context in addition to nucleophilic substitution reactions.

For meta benzyl compounds, it is preferred that the reactive functions reside on the benzylic carbon atom and that the same comprise a leaving group. For the alpha-amides, which are also preferred, the reactive functional group is also a leaving group, but may conveniently reside alpha to the carbonyl. Preferably, the leaving group is a halogen, such that the groups are alpha haloamides. Other appendage molecules and a wide variety of functional groups thereupon may be employed in accordance with the spirit of this invention.

Preferred scaffold molecules are those which possess at least two functional groups, at least one of which can react with appendage molecules. It is preferred that two or more functional groups be present such that great diversity of resulting species can be attained. Thus, scaffolds having two, three and more functional groups reactive with appendage molecules—either in the same chemical way or in different ways—are highly useful in the practice of this invention. Preferred scaffold species are di-nitrogen heterocycles as disclosed herein. Many other scaffold species can be used, however.

It is preferred to react a plurality of appendage molecules with the scaffold molecules and also, in some preferred cases, to provide a plurality of scaffold molecules for such reactions. The resulting compositions can be seen to be mixtures of reaction species. One preferred use for such mixtures is in the identification of chemical species which have biological activity, especially pharmaceutical activity. Such mixtures can be screened for activity and active molecular species determined. Such mixtures, conventionally denominated "libraries" are useful per se, and are well known to be useful in the chemical and pharmaceutical industry, where the preparation and exchange of libraries for screening is a common undertaking.

It will be appreciated that the present invention provides highly diverse libraries for this purpose in addition to the antibacterial activity shown by many such libraries.

It will also be appreciated that compounds contemplated by the present invention include modification of the species set forth herein. Thus, conjugates, oligomers, and other related species having the chemical properties called for are within the spirit of this invention.

EXAMPLES

In the following examples, THF refers to tetrahydrofuran and DMF refers to dimethylformamide. 2-Mercapto-1-ethanesulfonic acid (sodium salt),3-mercapto-1-propanesulfonic acid (sodium salt),1-phenylpiperazine,THF, DMF, diisopropylethylamine, and 2-aminoethanesulfonic acid were purchased from Aldrich (Milwaukee, Wis.), 2-aminobenzothiazole was purchased from Lancaster (Windham, N.H.), and bromoacetyl bromide was purchased from Fluka (Ronkonkoma, N.Y.). Rotary evaporations were performed in vacuo (50 torr) at 35° C. unless otherwise noted. NMR was performed on a Varian Geminii 200 or Varian Unity 400. Mass spectrometry were taken on a Hewlett Packard 59987A electrospray mass spectrometer (quadrupole mass analyzer 0–2600 amu).

For examples 1–18, R' represents a mixture of the following substituents:

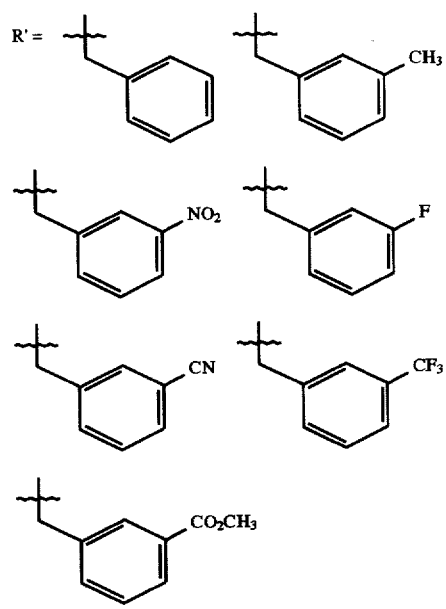

Example 1

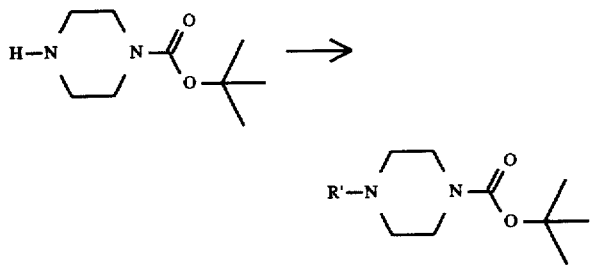

tert-Butyl 4-benzyl-1-piperazinecarboxylate (1), tert-Butyl 4-(3'-methylbenzyl)-1-piperazinecarboxylate (2), tert-Butyl 4-(3'-nitrobenzyl)-1-piperazinecarboxylate (3), tert-Butyl 4-(3'-fluorobenzyl)-1-piperazinecarboxylate (4), tert-Butyl 4-(3'-cyanobenzyl)-1-piperazinecarboxylate (5), tert-Butyl 4-(3'-trifluoromethylbenzyl)-1-piperazinecarboxylate (6) and tert-Butyl 4-(3'-methylcarboxylbenzyl)-1-piperazinecarboxylate (7)

To a solution of tert-butyl 1-piperazinecarboxylate (prepared as per the procedures of Essien, H., *J. Med. Chem.*, 1988, 31, 898) (0.56 g, 3 mmol) in THF (60 mL) was added a mixture of benzyl bromide (360 μL, 3 mmol), 3-methylbenzyl bromide (423 μL, 3 mmol), 3-trifluoromethylbenzyl bromide (460 μL, 3 mmol), 3-fluorobenzyl bromide (372 μL, 3 mmol), methyl 3-(bromomethyl) benzoate (0.72 g, 3 mmol), 3-cyanobenzyl bromide (0.66 g, 3 mmol) and 3-nitrobenzyl bromide (0.6 g, 3 mmol) in the presence of diisopropylethylamine (900 μL, 5.1 mmol). The reaction mixture was stirred at room temperature for 12 hours and then poured into an aqueous mixture of 3-mercapto-1-propanesulfonic acid, sodium salt (7.5 g, 42 mmol) and potassium carbonate (12 g, 84 mmol). The resulting mixture was stirred at room temperature for about 2 hours, concentrated in vacuo and partitioned between ether and water. The aqueous layer was separated and extracted with ether (2×30 mL). The organic layers were combined, dried over Na$_2$SO$_4$, filtered and concentrated in vacuo to afford a mixture of the title compounds (970 mg).

Mass spectrum: 277 [M+H]$^+$, 291 [M+H]$^+$, 345 [M+H]$^+$, 295 [M+H]$^+$, 335 [M+H]$^+$.

Example 2

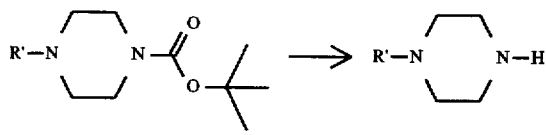

1-Benzylpiperazine (8), 1-(3'-methylbenzyl)piperazine (9), 1-(3'-nitrobenzyl)piperazine (10), 1-(3'-fluoromethylbenzyl) piperazine (11), 1-(3'-cyanobenzyl)piperazine (12), 1-(3'-trifluoromethylbenzyl)piperazine (13) and 1-(3'-methylcarboxylbenzyl)piperazine (14)

To the mixture from Example 1 (3 mmol) in ethanol (20 mL) was added 6M HCl in ethanol (30 mL, 180 mmol). The reaction mixture was stirred at room temperature for about 12 hours and concentrated in vacuo. The resulting residue was dissolved in water (20 mL), made basic with NaOH and extracted with ethyl acetate (2×30 mL). The organic layers were combined, dried over Na$_2$SO$_4$, filtered and concentrated in vacuo to afford the title mixture of deprotected compounds (570 mg, 2.72 mmol, 91%).

Mass spectrum: 177 [M+H]$^+$, 191 [M+H]$^+$, 195 [M+H]$^+$, 202 [M+H]$^+$, 222 [M+H]$^+$, 235 [M+H]$^+$ and 245 [M+H].

Example 3

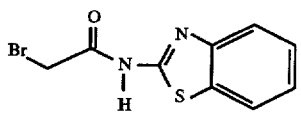

Bromo-N-(2'-benzothiazolyl)acetamide

The title compound was prepared via a modification of the literature procedure of Yuan, J.; Zhang, M., *Beijing Daxue Xuebao, Ziran Kexueban*, 1988, 24, 504–506. To a solution of 2-aminobenzothiazole (7.50 g, 50.0 mmol) in THF (250 mL) was added diisopropylethylamine (9.58 mL, 55.0 mmol). The resulting mixture was cooled to –20 ° C., and bromoacetyl bromide (4.78 mL, 55.0 mmol) was added slowly. The reaction mixture was warmed to room temperature over 30 minutes and stirred for an additional 30 minutes. The reaction mixture was diluted with water (100 mL), stirred for 30 minutes and further diluted with ethyl acetate (500 mL). The organic layer was separated, washed with water (2×100 mL), washed with brine (100 mL), dried over magnesium sulfate and concentrated in vacuo to afford a purple solid (14.96 g). Recrystallization of the crude product from ethyl acetate provided 8.30 g (61%) the title compound as a purple solid.

$^1$H-NMR (Me$_2$SO-d$_6$): δ 12.78 (br, 1H), 8.0–7.3 (m, 4H) and 4.22 (s, 2H). Mass spectrum (FAB+) m/z 271/273 [M+H]$^+$ Example 4

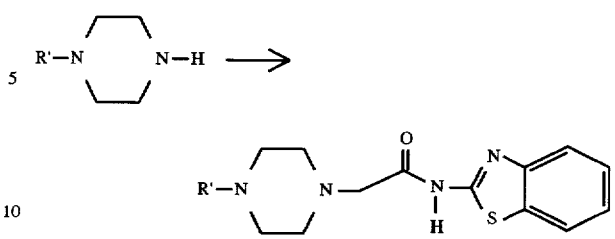

2-[4'-(Benzyl)piperazyl]-N-(2'-benzothiazolyl)acetamide (15), 2-[4'-(3"-methylbenzyl)piperazyl]-N-(2'-benzothiazolyl)acetamide (16), 2-[4'-(3"-nitrobenzyl) piperazyl]-N-(2'-benzothiazolyl)acetamide (17), 2-[4'-(3"-fluoromethylbenzyl)piperazyl]-N-(2'-benzothiazolyl) acetamide (18), 2-[4'-(3"-cyanobenzyl)piperazyl]-N-(2'-benzothiazolyl)acetamide (19), 2-[4'-(3"-trifluoromethylbenzyl)piperazyl]-N-(2'-benzothiazolyl) acetamide (20) and 2-[4'-(3"-methylcarboxylbenzyl) piperazyl]-N-(2'-benzothiazolyl)acetamide (21)

To a mixture of compounds 8–14 (Example 2) (0.45 mmol) in THF (10 mL) was added α-bromo-N-(2'-benzothiazolyl)acetamide (0.186 g, 0.69 mmol) in the presence of diisopropylethylamine (175 µL, 1 mmol). The reaction mixture was stirred at room temperature for 12 hours and then poured into a methanol-water solution containing 3-mercapto-1-propanesulfonic acid, sodium salt (0.125 g, 0.7 mmol) and potassium carbonate (0.2 g, 1.4 mmol). The resulting mixture was stirred at room temperature for 2 hours and concentrated in vacuo and partitioned between water and ether. The aqueous layer was separated and extracted with ether (2×30 mL). The organic layers were combined, dried over Na$_2$SO$_4$, filtered and concentrated to afford 160 mg (0.41 mmol, 90%) of the title mixture.

Mass Spectrum: ES/MS (367, 381, 385, 392, 412, 435).

Example 5

Bromo-N-cycloheptyl acetamide

To a –20° C. solution of cycloheptylamine (6.37 mL, 50.0 mmol) and diisopropylethylamine (9.58 mL, 55.0 mmol) in methylene chloride (250 mL) was slowly added bromoacetyl bromide (4.78 mL, 55.0 mmol). The reaction mixture was warmed to room temperature over 20 minutes and stirred for an addition 30 minutes. The reaction mixture was diluted with water (100 mL) and stirred for an additional 30 minutes. The organic layer was separated, washed with water (3×100 mL), dried over magnesium sulfate and concentrated in vacuo to afford a beige solid (10.5 g). The crude material was further purified by silica gel flash column chromatography using hexane-ethyl acetate (1:1) as the eluent to give the purified title compound as a white solid (9.77 g, 83%).

$^1$H-NMR (Me$_2$SO-d$_6$): δ 8.20 (br d, 1H), 3.77 (s, 2H), 3.67 (m, 1H) and 1.8-1.3 (m, 12H). $^{13}$C-NMR (CDCl$_3$): δ 164.01, 51.04, 34.59, 29.40, 27.80 and 23.87. Mass spectrum (FAB+) m/z 234/236 [M+H]$^+$ and 256/258 [M+Na]$^+$.

Example 6

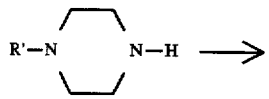

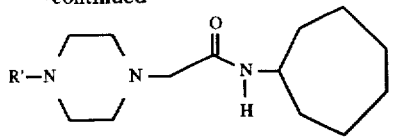

2-[4'-(Benzyl)piperazyl]-N-cycloheptyl acetamide (22), 2-[4'-(3"-methylbenzyl)piperazyl]-N-cycloheptyl acetamide (23), 2-[4'-(3"-nitrobenzyl)piperazyl]-N-cycloheptyl acetamide (24), 2-[4'-(3"-fluoromethylbenzyl)piperazyl]-N-cycloheptyl acetamide (25), 2-[4'-(3"-cyanobenzyl)piperazyl]-N-cycloheptyl acetamide (26), 2-[4'-(3"-trifluoromethylbenzyl)piperazyl]-N-cycloheptyl acetamide (27) and 2-[4'-(3"-methylcarboxylbenzyl)piperazyl]-N-cycloheptyl acetamide (28)

To the mixture of compounds 8–14 (Example 2) (0.45 mmol) in THF (10 mL) was added α-bromo-N-cycloheptyl acetamide (0.186 g, 0.69 mmol) in the presence of diisopropylethylamine (175 μL, 1 mmol). The reaction mixture was stirred at room temperature for 12 hours and then poured into a methanol-water solution containing 3-mercapto-1-propanesulfonic acid, sodium salt (0.125 g, 0.7 mmol) and potassium carbonate (0.2 g, 1.4 mmol). The resulting mixture was stirred at room temperature for about 2 hours and concentrated in vacuo and partitioned between water and ether. The aqueous layer was separated and extracted with ether (2×30 mL). The organic layers were combined, dried over $Na_2SO_4$, filtered and concentrated to afford 150 mg (0.42 mmol, 92%) of the title mixture.

Mass Spectrum: ES/MS (330, 344, 348, 355, 375, 398).

Example 7
Bromo-N-(benzyloxyl)acetamide

To a 0° C. solution of O-benzylhydroxylamine hydrochloride (1.6 g, 10 mmol) in THF (40 mL) was added bromoacetyl bromide (871 μL, 10 mmol) and diisopropylethylamine (3.5 mL, 20 mmol). The reaction mixture was warmed to room temperature overnight and diluted with ethyl acetate and water. The aqueous layer was separated and extracted with ethyl acetate. The organic layers were combined, dried over $Na_2SO_4$, filtered and concentrated in vacuo. The crude material was purified by silica gel flash column chromatography with ethyl acetate-hexane to give 1.27 g (52%) of the title compound.

TLC ($R_f$=0.5; 40% ethyl acetate-hexane). $^1H$ NMR (CDCl3): δ 9.21 (br s, 1H, NH), 7.31 (s, 5H, Ar), 4.84 (s, 2H, CH2) and 3.89 (s, 2H, CH2). $^{13}C$ NMR (CDCl3): δ 163.7, 134.4, 129.5, 129.3, 128.9, 128.6, 78.5 and 40.3.

Example 8

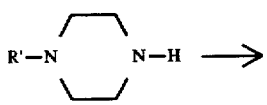

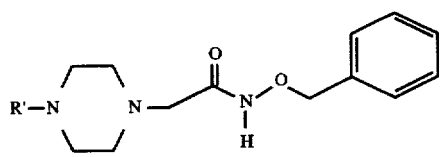

2-[4'-(Benzyl)piperazyl]-N-(O-benzylhydroxyl)acetamide (29), 2-[4'-(3"-methylbenzyl)piperazyl]-N-(O-benzylhydroxyl)acetamide (30), 2-[4'-(3"-nitrobenzyl)piperazyl]-N-(O-benzylhydroxyl)acetamide (31), 2-[4'-(3"-fluoromethylbenzyl)piperazyl]-N-(O-benzylhydroxyl)acetamide (32), 2-[4'-(3"-cyanobenzyl)piperazyl]-N-(O-benzylhydroxyl)acetamide (33), 2-[4'-(3"-trifluoromethylbenzyl)piperazyl]-N-(O-benzylhydroxyl)acetamide (34) and 2-[4'-(3"-methylcarboxylbenzyl)piperazyl]-N-(O-benzylhydroxyl)acetamide (35)

To the mixture of compounds 8–14 (Example 2) (0.49 mmol) in THF (10 mL) was added bromo-N-(O-benzylhydroxyl)acetamide (0.2 g, 0.8 mmol) in the presence of diisopropylethylamine (520 μL, 3 mmol). The reaction mixture was stirred at room temperature for 12 hours and then poured into a methanol-water solution containing 3-mercapto-1-propanesulfonic acid, sodium salt (0.23 g, 1.3 mmol) and potassium carbonate (0.4 g, 2.6 mmol). The resulting mixture was stirred at room temperature for about 2 hours and concentrated in vacuo and partitioned between water and ether. The aqueous layer was separated and extracted with ether (2×30 mL). The organic layers were combined, dried over $Na_2SO_4$, filtered and concentrated to afford 150 mg (0.42 mmol, 92%) of the title mixture as an oil.

Mass Spectrum: ES/MS (340, 354, 408, 358, 365, 385).

Example 9

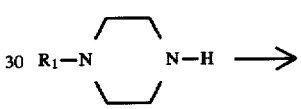

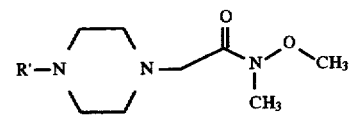

2-[4'-(Benzyl)piperazyl]-N-methoxy-N-methylacetamide (36), 2-[4'-(3"-methylbenzyl)piperazyl]-N-methoxy-N-methylacetamide (37), 2-[4'-(3"-nitrobenzyl)piperazyl]-N-methoxy-N-methylacetamide (38), 2-[4'-(3"-fluoromethylbenzyl)piperazyl]-N-methoxy-N-methylacetamide (39), 2-[4'-(3"-cyanobenzyl)piperazyl]-N-methoxy-N-methylacetamide (40), 2-[4'-(3"-trifluoromethylbenzyl)piperazyl]-N-methoxy-N-methylacetamide (41) and 2-[4'-(3"-methylcarboxylbenzyl)piperazyl]-N-methoxy-N-methylacetamide (42)

To the mixture of compounds 8–14 (Example 2) (0.49 mmol) in THF (10 mL) was added 2-chloro-N-methoxy-N-methylacetamide (0.12 g, 0.85 mmol) in the presence of diisopropylethylamine (525 μL, 3 mmol). The reaction mixture was stirred at room temperature for 12 hours and at reflux for 6 hours. The reaction mixture was cooled to room temperature and poured into a methanol-water solution containing 3-mercapto-1-propanesulfonic acid, sodium salt (0.3 g, 1.7 mmol) and potassium carbonate (0.5 g, 3.4 mmol). The resulting mixture was stirred at room temperature for about 2 hours and concentrated in vacuo and partitioned between water and ether. The aqueous layer was separated and extracted with ether (2×30 mL). The organic layers were combined, dried over $Na_2SO_4$, filtered and concentrated to afford 87.3 mg (0.283 mmol, 58%) of the title mixture as an oil.

Mass Spectrum: ES/MS (278, 292, 296, 303, 323, 346).

Example 10

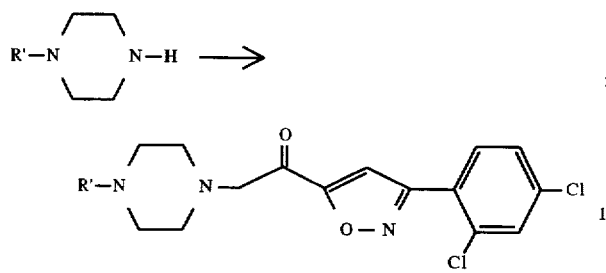

5-[4'-(Benzyl)piperazyl]acetyl-3-(2',4'-dichlorophenyl) isoxazole (43), 5-[4'-(3"-methylbenzyl)piperazyl]acetyl-3-(2',4'-dichlorophenyl)isoxazole (44), 2-[4'-(3"-nitrobenzyl) piperazyl]acetyl-3-(2',4'-dichlorophenyl)isoxazole (45), 2-[4'-(3"-fluoromethylbenzyl)piperazyl]acetyl-3-(2',4'-dichlorophenyl)isoxazole (46), 2-[4'-(3"-cyanobenzyl) piperazyl]acetyl-3-(2',4'-dichlorophenyl)isoxazole (47), 2-[4'-(3"-trifluoromethylbenzyl)piperazyl]acetyl-3-(2',4'-dichlorophenyl)isoxazole (48) and 2-[4'-(3"-methylcarboxylbenzyl)piperazyl]acetyl-3-(2',4'-dichlorophenyl)isoxazole (49)

To the mixture of compounds 8–14 (Example 2) (0.45 mmol) in THF (5 mL) was added 5-(bromoacetyl)-3-(2',4'-dichlorophenyl)isoxazole (0.015 g, 0.045 mmol) in the presence of diisopropylethylamine (20 µL, 0.09 mmol). The reaction mixture was stirred at room temperature for 12 hours and then concentrated in vacuo. The resultant residue was diluted with 1M HCl solution (20 mL) and extracted with ether (2×30 mL). The organic layers were combined, dried over $Na_2SO_4$, filtered and concentrated to afford 18.1 mg (0.035 mmol, 77.8%) of the title mixture as an oil.

Mass spectrum: ES/MS (475, 489, 543, 493, 500, 520).

Example 11

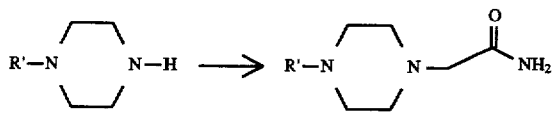

2-[4'-(Benzyl)piperazyl]acetamide (50),2-[4'-(3"-methylbenzyl)piperazyl]acetamide (51), 2-[4'-(3"-nitrobenzyl)piperazyl]acetamide (52), 2-[4'-(3"-fluoromethylbenzyl)piperazyl]acetamide (53), 2-[4'-(3"-cyanobenzyl)piperazyl]acetamide (54), 2-[4'-(3"-trifluoromethylbenzyl)piperazyl]acetamide (55) and 2-[4'-(3"-methylcarboxylbenzyl)piperazyl]acetamide (56)

To the mixture of compounds 8–14 (Example 2) (1.29 g, 1.3 mmol) in THF (30 mL) was added α-bromoacetamide (0.28 g, 2 mmol) in the presence of diisopropylethylamine (460 µL, 2.6 mmol). The reaction mixture was stirred at room temperature for 12 hours and poured into a methanol-water solution containing 3-mercapto-1-propanesulfonic acid, sodium salt (0.17 g, 1 mmol) and potassium carbonate (0.3 g, 2 mmol). The resulting mixture was stirred at room temperature for 2 hours, concentrated in vacuo and partitioned between water and ether. The aqueous layer was separated and extracted with ether (2×30 mL). The organic layers were combined, dried over $Na_2SO_4$, filtered and concentrated to afford 210 mg (0.8 mmol, 62%) of the title mixture as an oil.

Mass spectrum: ES/MS (234, 248, 252, 259, 279, 302).

Example 12

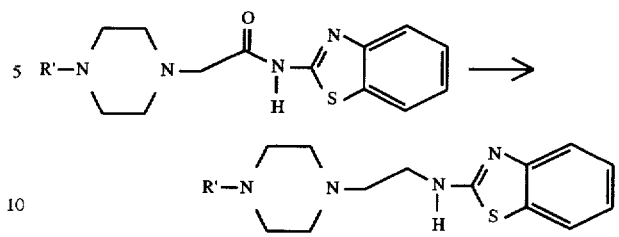

4-[2'-(N-Benzothiazol-2"-yl)amino]ethyl-1-benzyl piperazine (57), 4-[2'-(N-benzothiazol-2"-yl)amino]ethyl-1-(3'-methylbenzyl)piperazine (58), 4-[2'-(N-benzothiazol-2"-yl) amino]ethyl-1-(3'-nitrobenzyl)piperazine (59), 4-[2'-(N-benzothiazol-2"-yl)amino]ethyl-1-(3'-fluoromethylbenzyl) piperazine (60), 4-[2'-(N-benzothiazol-2"-yl)amino]ethyl-1-(3'-cyanobenzyl)piperazine (61), 4-[2'-(N-benzothiazol-2"-yl)amino]ethyl-1-(3'-trifluoromethylbenzyl)piperazine (62) and 4-[2'-(N-benzothiazol-2"-yl)amino]ethyl-1-(3'-methylcarboxylbenzyl)piperazine (63)

To the mixture of compounds 15–21 (Example 4) (0.405 mmol) in THF (10 mL) was added a 1M solution of $BH_3$ in THF (10 mL, 10 mmol). The mixture was stirred at reflux temperature for 24 hours and cooled to room temperature. The reaction mixture was diluted with a 6M HCl solution (5 mL), stirred at room temperature for 1 hour and concentrated in vacuo. The resultant residue was dissolved in water (20 mL), basified with NaOH and extracted with ethyl acetate (2×20 mL). The organic layers were combined, dried over $Na_2SO_4$, filtered and concentrated to afford 100 mg (0.262 mmol, 64.7%) as an oil.

Mass spectrum: ES/MS (353, 367, 371, 382, 398, 421).

Example 13

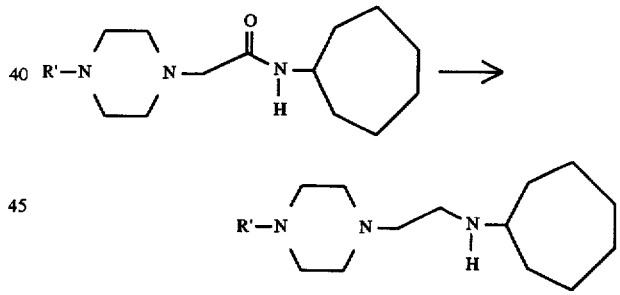

4-[2'-(N-cycloheptyl)amino]ethyl-1-benzyl piperazine (64), 4-[2'-(N-cycloheptyl)amino]ethyl-1-(3'-methylbenzyl) piperazine (65), 4-[2'-N-cycloheptyl)amino]ethyl-1-(3'-nitrobenzyl)piperazine (66), 4-[2'-(N-cycloheptyl)amino] ethyl-1-(3'-fluoromethylbenzyl)piperazine (67), 4-[2'-(N-cycloheptyl)amino]ethyl-1-(3'-cyanobenzyl)piperazine (68), 4-[2'-(N-cycloheptyl)amino]ethyl-1-(3'-trifluoromethylbenzyl)piperazine (69) and 4-[2'-(N-cycloheptyl)amino]ethyl-1-(3'-methylcarboxylbenzyl) piperazine (70)

To the mixture of compounds 22–28 (Example 6) (0.41 mmol) in THF (10 mL) was added a 1M solution of $BH_3$ in THF (10 mL, 10 mmol). The mixture was stirred at reflux temperature for 24 hours and cooled to room temperature. The reaction mixture was diluted with a 6M HCl solution (5 mL), stirred at room temperature for 1 hour and concentrated in vacuo. The resultant residue was dissolved in water (20 mL), basified with NaOH and extracted with ethyl acetate (2×20 mL). The organic layers were combined, dried over Na$_2$SO$_4$, filtered and concentrated to afford 114 mg (0.33 mmol, 80.7%) of the title mixture as an oil.

Mass spectrum: ES/MS (316, 330, 334, 342, 361, 384).

Example 14

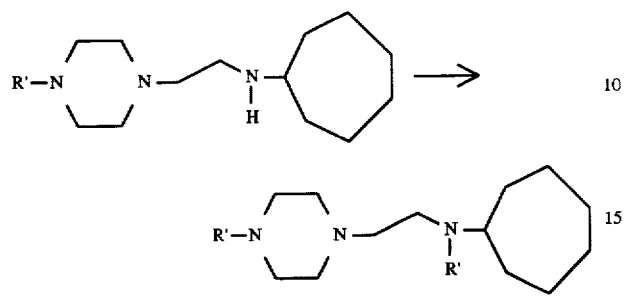

Compounds 106–154

To the mixture of compounds 64–70 (Example 13) (0.023 mmol) in THF (3 mL) was added a mixture of benzyl bromide (3 mL, 0.023 mmol), 3-methylbenzyl bromide (3.2 mL, 0.023 mmol), 3-trifluoromethylbenzyl bromide (3.5 mL, 0.023 mmol), 3-fluorobenzyl bromide (3 mL, 0.023 mmol), 3-cyanobenzyl bromide (5.1 mg, 0.023 mmol) and 3-nitrobenzyl bromide (5 mg, 0.023 mmol) in the presence of diisopropylethylamine (10 mL, 0.046 mmol). The mixture was stirred at room temperature for 12 hours and at reflux for 6 hours. The reaction mixture was cooled to room temperature and poured into a methanol-water solution containing 3-mercapto-1-propanesulfonic acid, sodium salt (0.05 g, 0.28 mmol) and potassium carbonate (0.08 g, 0.58 mmol). The resulting mixture was stirred at room temperature for 2 hours, concentrated in vacuo and partitioned between water and ether. The aqueous layer was separated and extracted with ether (2×20 mL). The organic layers were combined, dried over Na$_2$SO$_4$, filtered and concentrated to afford 8.4 mg (0.0182 mmol, 79%) of the title library as an oil.

Mass spectrum: ES/MS (406, 420, 424, 431, 434, 438, 442, 445, 451, 465, 469, 474, 488, 492, 499, 519, 542).

Example 15

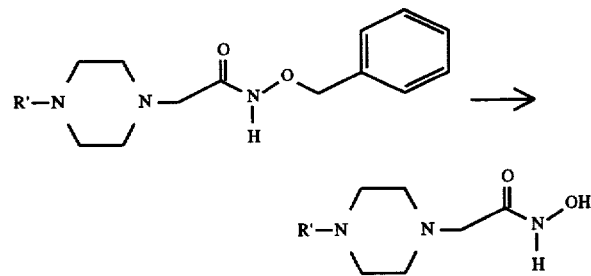

2-[4'-(Benzyl)piperazyl]-N-hydroxyl acetamide (71), 2-[4'-(3''-methylbenzyl)piperazyl]-N-hydroxyl acetamide (72), 2-[4'-(3''-nitrobenzyl)piperazyl]-N-hydroxyl acetamide (73), 2-[4'-(3''-fluoromethylbenzyl)piperazyl]-N-hydroxyl acetamide (74), 2-[4'-(3''-cyanobenzyl)piperazyl]-N-hydroxyl acetamide (75), 2-[4'-(3''-trifluoromethylbenzyl)piperazyl]-N-hydroxyl acetamide (76) and 2-[4'-(3''-methylcarboxylbenzyl)piperazyl]-N-hydroxyl acetamide (77).

To a mixture compounds 29–35 (0.022 g, 0.062 mmol) in methanol (10 mL) was added 5% palladium on activated carbon (20 mg). The reaction mixture was placed under an atmosphere of hydrogen and stirred at room temperature for 12 hours. The reaction mixture was filtered through a pad of Celite and concentrated to afford 8.2 mg (0.03 mmol, 48.4%) of the title mixture as an oil.

Example 16

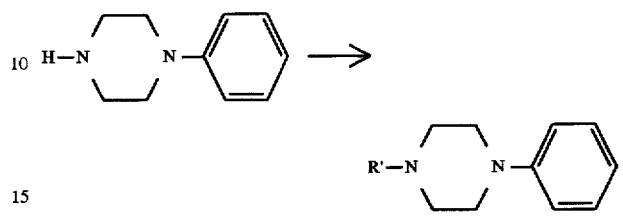

1-Benzyl-4-phenyl piperazine (78), 1-(3'-methylbenzyl)-4-phenyl piperazine (79), 1-(3'-nitrobenzyl)-4-phenyl piperazine (80), 1-(3'-fluorobenzyl)-4-phenyl piperazine (81), 1-(3'-cyanobenzyl)-4-phenylpiperazine (82), 1-(3'-trifluoromethylbenzyl)-4-phenyl piperazine (83) and 1-(3'-methylcarboxylbenzyl)-4-phenyl piperazine (84)

To a solution of N-phenyl piperazine (45 mL, 0.29 mmol) in THF (10 mL) was added a mixture of benzyl bromide (36 mL, 0.3 mmol), 3-methylbenzyl bromide (42.3 mL, 0.3 mmol), 3-trifluoromethylbenzyl bromide (46 mL, 0.3 mmol), 3-fluorobenzyl bromide (37 mL, 0.3 mmol), methyl 3-(bromomethyl)benzoate (0.072 g, 0.3 mmol), 3-cyanobenzyl bromide (0.066 g, 0.3 mmol) and 3-nitrobenzyl bromide (0.06 g, 0.3 mmol) in the presence of diisopropylethylamine (100 mL, 0.5 mmol). The reaction mixture was stirred at room temperature for 12 hours and then poured into a methanol-water solution containing 3-mercapto-1-propanesulfonic acid, sodium salt (0.5 g, 3.15 mmol) and potassium carbonate (1 g, 7 mmol). The mixture was stirred at room temperature for 2 hours and concentrated. The resulting residue was partitioned between ether and water. The aqueous layer was separated and extracted with ether (2×30 mL). The organic layers were combined, washed with brine, dried over Na$_2$SO$_4$, filtered and concentrated to afford 130 mg of the title library as an oil.

Mass spectrum: ES/MS (253, 267, 271, 278, 298, 311, 321).

Example 17

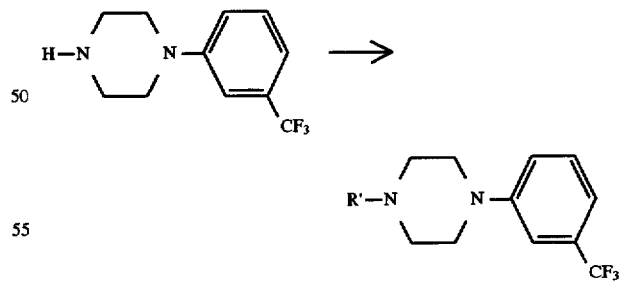

1-Benzyl-4-(3'-trifluoromethylphenyl) piperazine (85), 1-(3'-methylbenzyl)-4-(3'-trifluoromethylphenyl) piperazine (86), 1-(3'-nitrobenzyl)-4-(3'-trifluoromethylphenyl) piperazine (87), 1-(3'-fluorobenzyl)-4-(3'-trifluoromethylphenyl) piperazine (88), 1-(3'-cyanobenzyl)4-(3'-trifluoromethylphenyl)piperazine (89), 1-(3'-trifluoromethylbenzyl)-4-(3'-trifluoromethylphenyl) piperazine (90) and 1-(3'-methylcarboxylbenzyl)-4-(3'-trifluoromethylphenyl)piperazine (91)

To a solution of 1-(3'-trifluoromethylphenyl) piperazine (55 mL, 0.29 mmol) in THF (10 mL) was added mixture of benzyl bromide (36 mL, 0.3 mmol), 3-methylbenzyl bromide (42.3 mL, 0.3 mmol), 3-trifluoromethylbenzyl bromide (46 mL, 0.3 mmol), 3-fluorobenzyl bromide (37 mL, 0.3 mmol), methyl 3-(bromomethyl)benzoate (0.072 g, 0.3 mmol), 3-cyanobenzyl bromide (0.066 g, 0.3 mmol) and 3-nitrobenzyl bromide (0.06 g, 0.3 mmol) in the presence of diisopropylethylamine (100 mL, 0.5 mmol). The reaction mixture was stirred at room temperature for 12 hours and then poured into a methanol-water solution containing 3-mercapto-1-propanesulfonic acid, sodium salt (0.5 g, 3.15 mmol) and potassium carbonate (1 g, 7 mmol). The mixture was stirred at room temperature for 2 hours and concentrated. The resulting residue was partitioned between ether and water. The aqueous layer was separated and extracted with ether (2×30 mL). The organic layers were combined, washed with brine, dried over Na₂SO₄, filtered and concentrated to afford the title library as an oil (89.1 mg, 0.252 mmol, 87.1%).

Mass spectrum: ES/MS (321, 335, 339, 346, 366, 379, 389).

Example 18

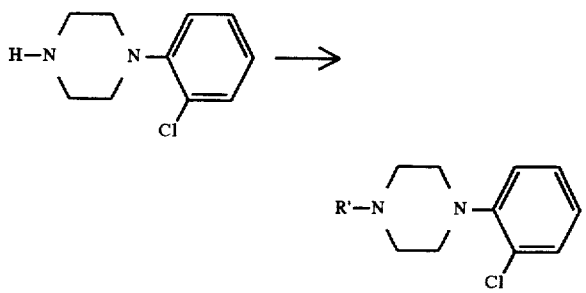

1-Benzyl-4-(2'-chlorophenyl) piperazine (92), 1-(3'-methylbenzyl)4-(2'-chlorophenyl) piperazine (93), 1-(3'-nitrobenzyl)-4-(2'-chlorophenyl) piperazine (94), 1-(3'-fluorobenzyl)-4-(2'-chlorophenyl) piperazine (95), 1-(3'-cyanobenzyl)-4-(2'-chlorophenyl) piperazine (96), 1-(3'-trifluoromethylbenzyl)-4-(2'-chlorophenyl) piperazine (97) and 1-(3'-methylcarboxylbenzyl)-4-(2'-chlorophenyl) piperazine (98)

To a solution of 1-(2-chlorophenyl)piperazine monohydrochloride (67 mg, 0.29 mmol) in THF (10 mL) was added a mixture of benzyl bromide (36 mL, 0.3 mmol), 3-methylbenzyl bromide (42.3 mL, 0.3 mmol), 3-trifluoromethylbenzyl bromide (46 mL, 0.3 mmol), 3-fluorobenzyl bromide (37 mL, 0.3 mmol), methyl 3-(bromomethyl)benzoate (0.072 g, 0.3 mmol), 3-cyanobenzyl bromide (0.066 g, 0.3 mmol) and 3-nitrobenzyl bromide (0.06 g, 0.3 mmol) in the presence of diisopropylethylamine (200 mL, 1 mmol). The reaction mixture was stirred at room temperature for 12 hours and then poured into a methanol-water solution containing 3-mercapto-1-propanesulfonic acid, sodium salt (0.5 g, 3.15 mmol) and potassium carbonate (1 g, 7 mmol). The mixture was stirred at room temperature for 2 hours and concentrated. The resulting residue was partitioned between ether and water. The aqueous layer was separated and extracted with ether (2×30 mL). The organic layers were combined, washed with brine, dried over Na₂SO₄, filtered and concentrated to afford 79 mg (0.247 mmol, 85.2%) of the title library as an oil.

Mass spectrum: ES/MS 287, 301, 305, 312, 332, 345, 355.

Example 19

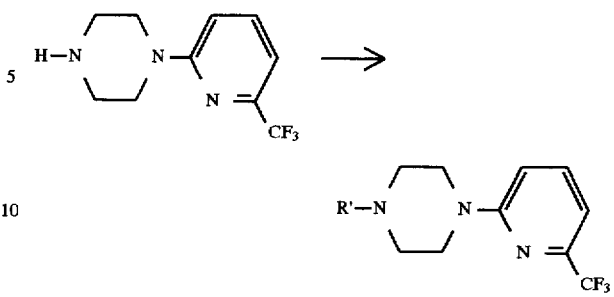

1-Benzyl-4-[6'-(trifluoromethyl)pyrid-2'-yl] piperazine (99), 1-(3'-methylbenzyl)4-[6'-(trifluoromethyl)pyrid-2'-yl] piperazine (100), 1-(3'-nitrobenzyl)4-[6'-(trifluoromethyl)pyrid-2'-yl] piperazine (101), 1-(3'-fluorobenzyl)4-[6'-(trifluoromethyl)pyrid-2'-yl] piperazine (102), 1-(3'-cyanobenzyl)-4-[6'-(trifluoromethyl)pyrid-2'-yl] piperazine (103), 1-(3'-trifluoromethylbenzyl)-4-[6'-(trifluoromethyl)pyrid-2'-yl] piperazine (104) and 1-(3'-methylcarboxylbenzyl)-4-[6'-(trifluoromethyl)pyrid-2'-yl] piperazine (105)

To a solution of 1-[6-(trifluoromethyl)pyrid-2'-yl] piperazine (0.069 g, 0.3 mmol) in THF (10 mL) was added a mixture of benzyl bromide (36 mL, 0.3 mmol), 3-methylbenzyl bromide (42.3 mL, 0.3 mmol), 3-trifluoromethylbenzyl bromide (46 mL, 0.3 mmol), 3-fluorobenzyl bromide (37 mL, 0.3 mmol), methyl 3-(bromomethyl)benzoate (0.072 g, 0.3 mmol), 3-cyanobenzyl bromide (0.066 g, 0.3 mmol) and 3-nitrobenzyl bromide (0.06 g, 0.3 mmol) in the presence of diisopropylethylamine (100 mL, 0.5 mmol). The reaction mixture was stirred at room temperature for 12 hours and then poured into a methanol-water solution containing 3-mercapto-1-propanesulfonic acid, sodium salt (0.5 g, 3.15 mmol) and potassium carbonate (1 g, 7 mmol). The mixture was stirred at room temperature for 2 hours and concentrated. The resulting residue was partitioned between ether and water. The aqueous layer was separated and extracted with ether (2×30 mL). The organic layers were combined, washed with brine, dried over Na₂SO₄, filtered and concentrated to afford 98.3 mg (0.28 mmol, 93.3%) of the title library as an oil.

Mass spectrum: ES/MS (322, 336, 340, 347, 367, 380, 390).

Example 20

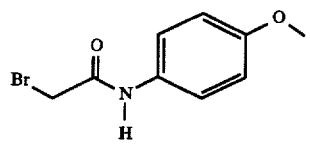

Bromo-N-(4-methoxyphenyl) acetamide

The title compound was prepared via a modification of the literature procedure (Vloon, W. J.; Kruk, C.; Pandit, U. K.; Hofs, H. P.; McVie, J. G. *J. Med. Chem.* 1987, 30, 20–4.). To a solution of 4-methoxyaniline (4.93 g, 40.0 mmol) in methylene chloride (200 mL) was added diisopropylethylamine (7.66 mL, 44.0 mmol). The resulting mixture was cooled to −20° C., and bromoacetyl bromide (3.82 mL, 44.0 mmol) was added slowly. The reaction mixture was warmed to room temperature over 20 minutes and stirred additional 30 minutes. The reaction mixture was diluted with water (100 mL), stirred for 30 minutes and the organic layer was separated. The organic layer was washed with water (2×100 mL), brine (100 mL), dried over magnesium sulfate and concentrated in vacuo to afford a beige solid (9.68 g) which was recrystallized from ethyl acetate to provide bromo-N-(4'-methoxyphenyl) acetamide as a white crystal (6.31 g, 65%).

Example 21

where each R' and R" are independently:

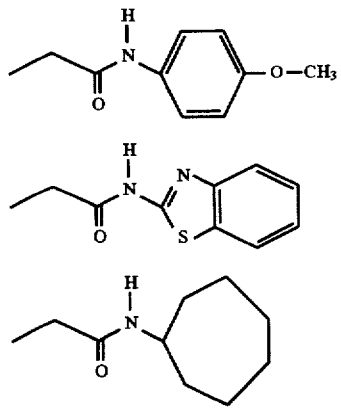

Compounds 155–160

A solution of piperazine (0.056 g, 0.65 mmol) in THF (20 mL) was treated with a mixture of bromo N-cycloheptyl acetamide (0.094 g, 0.4 mmol), bromo N-(benzothiazol-2'-yl) acetamide (0.094 g, 0.4 mmol) and bromo N-(4'-methoxyphenyl) acetamide (0.11 g, 0.4 mmol) in the presence of diisopropylethylamine (320 μL, 1.8 mmol). The mixture was stirred at room temperature for 12 hours. The reaction mixture was then poured into a methanol-water solution of 3-mercapto-1-propanesulfonic acid, sodium salt (0.43 g, 2.4 mmol) and potassium carbonate (0.7 g, 4.8 mmol). The mixture was stirred at room temperature for 2 hours and concentrated in vacuo. The resultant residue was partitioned between ether/H$_2$O and extracted with ether (2×30 mL). The organic layer was dried (Na$_2$SO$_4$), filtered and concentrated in vacuo to give the title group of compounds 220 mg (0.52 mmol, 80%) as an oily residue. The title group of compounds was further identified by ES/MS (413, 467, 393, 403, 430, 440).

Example 22

where each R' and R" are independently:

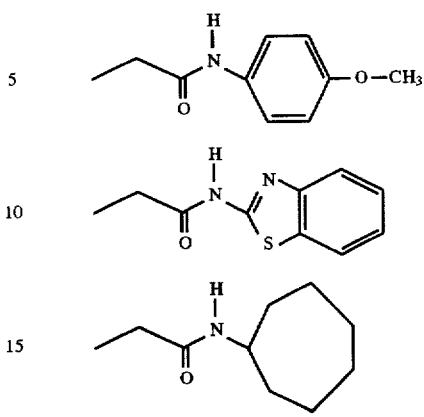

Compounds 161–166

A mixture of solution of compounds in Example 4 (160 mg, 0.52 mmol) in THF (30 mL) was treated with 1M BH$_3$/THF (2.08 mmol, 2 mL) under an atmosphere of argon. The mixture was stirred at reflux temperature for 12 hours. The reaction mixture was cooled to room temperature and 6M HCl solution (2 mL) was added. The mixture was stirred at room temperature for about 30 minutes and concentrated in vacuo. The resultant residue was dissolved in H$_2$O (20 mL), basified with NaOH and extracted with ether (2×30 mL). The organic layer was dried (Na$_2$SO$_4$), filtered and concentrated in vacuo to give the title group of compounds 117 mg (0.29 mmol, 77%) as an oily residue. The title group of compounds was further identified by ES/MS (365, 375, 385, 402, 412, 439).

EVALUATION

PROCEDURE 1

Antimicrobial Assay

*Staphylococcus aureus*

*Staphylococcus aureus* is known to cause localized skin infections as a result of poor hygiene, minor trauma, psoriasis or eczema. It also causes respiratory infections, pneumonia, toxic shock syndrome and septicemia. It is a common cause of acute food poisoning. It exhibits rapid emergence of drug resistance to penicillin, cephalosporin, vancomycin and nafcillin.

In this assay, the strain *S. aureus* ATCC 25923 (American Type Culture Collection) is used in the bioassay. To initiate the exponential phase of bacterial growth prior to the assay, a sample of bacteria grown overnight at 37° C. in typtocase soy broth (BBL). This bacteria is then used to reinoculate sample wells of 96-well microtiter plates. The assays are carried out in the 96-well microtiter plates in 150 μL volume with approximately 1×10$^6$ cells per well.

Bacteria in typtocase soy broth (75 μL) is added to the compound mixtures in solution in 75 μL water/4% DMSO in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

PROCEDURE 2
Antimicrobial Assays
A. Streptococcus Pyrogenes

In this assay, the strain *S. aureus* ATCC 14289 (American Type Culture Collection) is used in the bioassay. To initiate the exponential phase of bacterial growth prior to the assay, a sample of bacteria is grown overnight at 37° C. in 1x Todd-Hewitt broth. This bacteria is then used to reinoculate sample wells of 96-well microtiter plates. The assays are carried out in the 96-well microtiter plates in 150 μL volume with approximately $1 \times 10^6$ cells per well.

Bacteria in 1x Todd-Hewitt broth (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

B. E. coli imp-

In this assay, the strain *E. coli imp-* obtained from Spenser Bensen (Sampson, B. A., Misra, R. & Benson, S. A. (1989), *Genetics*, 122, 491–501, Identification and characterization of a new gene of *Escherichia coli* K-12 involved in outer membrane permeability) is used. To initiate the exponential phase of bacterial growth prior to the assay, a sample of bacteria is grown overnight at 37° C. in Luria broth. This bacteria is then used to reinoculate sample wells of 96-well microtiter plates. The assays are carried out in the 96-well microtiter plates in 150 μL volume with approximately $1 \times 10^6$ cells per well.

Bacteria in Luria broth (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Ampicillin and tetracycline antibiotic positive controls are concurrently tested in each screening assay.

Combinatorial libraries in accordance with the present invention have been tested for antibacterial activity utilizing assays that determine the minimum inhibitory concentration (MIC). The antibacterial assays utilize *streptococcus pyogenes* and *escherichia coli imp-*. Activity has been detected in a number of libraries of the present invention.

The following data are for first round libraries or parent libraries that were assayed for activity in accordance with the methods illustrated in Procedures 2A and 2B.

| Compounds | S. pyrogenes (μM) | E. coli (μM) | |
|---|---|---|---|
| 15–21 | 50–100 | 50–100 | (Ex. 4) |
| 22–28 | 25–50 | 50–100 | (Ex. 6) |
| 106–154 | 12.5–25 | 25–50 | (Ex. 14) |

In addition, compounds 155–160 (Ex. 21) exhibited 50% inhibition of *S.pyrogenes* at 100 μM and 30% inhibition of *E.coli* at 50 μM. Compounds 161–166 (Ex. 22) exhibited 70% inhibition of *S.pyrogenes* at 100 μM and 30% inhibition of *E.coli* at 50 μM.

The minimum inhibitory concentration (MIC) exhibited by a mixture of compounds containing 1-[2'-(N-benzothiazol-2"-yl)amino]ethyl4-alkaryl piperazine where alkaryl is benzyl, m-methylbenzyl, m-nitrobenzyl, m-fluorobenzyl, m-cyanobenzyl, m-trifluoromethylbenzyl and m-methylcarboxylbenzyl is 50–100 μM for both gram-positive bacteria, *E Coli* and gram-negative bacteria, *S. Pyogenes*. The MIC exhibited by a mixture of compounds containing 1-[2'-(N-cycloheptyl)amino]ethyl-4-alkaryl piperazine is 50–100 μM for gram-positive bacteria, *E. Coli* and 25–50 μM for gram-negative bacteria, *S. Pyogenes*. The MIC exhibited by a mixture of compounds containing 1-[2'-(N-cycloheptyl-N-alkaryl)amino]ethyl-4-alkaryl piperazine is 25–50 μM for gram-positive bacteria, *E. Coli* and 12.5–25 μM for gram-negative bacteria, *S. Pyogenes*.

PROCEDURE 3
Antifungal Assay
C. albicans

In this assay, the strain *C. albicans* ATCC 10231 (American Type Culture Collection) is used in the bioassay. To initiate the exponential phase of yeast growth prior to the assay, a sample of yeast is grown overnight at 37° C. in YM media. This yeast is then used to reinoculate sample wells of 96-well microtiter plates. The assays are carried out in the 96-well microtiter plates in 150 μL volume with approximately $1 \times 10^6$ cells per well.

Yeast in YM media (75 μL) is added to the compound mixtures in solution in 75 μL water in the individual well of the microtiter plate. Final concentrations of the compound mixtures are 25 μM, 10 μM and 1 μM. Each concentration of the compound mixtures are assayed in triplicate. The plates are incubated at 37° C. and growth monitored over a 24 hour period by measuring the optical density at 595 nm using a BioRad model 3550 UV microplate reader. The percentage of growth relative to a well containing no compound is determined. Amphotericin B positive control is concurrently tested in each screening assay.

PROCEDURE 4
RNA Binding Assay
The effect of libraries on tat/TAR interactions The effects of combinatorial libraries on tat/TAR, RNA/protein interactions are examined using a rapid and reproducible binding assay. The assay consists of a biotinylated truncated version of the HIV-1 TAR stem-loop, which is anchored to the wells of a 96 well ELISA plate which has been coated with streptavidin. The TAR RNA is recognized by the HIV-1 protein tat and the amount of tat bound is quantitated using an antibody raised against tat and a secondary antibody conjugated to an alkaline phosphatase or HRP enzyme to produce a colorimetric reaction.

Materials:

A 39 residue tat peptide (aa 49-85 of HIV tat protein). This is the C terminal basic binding domain of the tat protein. This peptide was synthesized by a contract lab.

A 30 base RNA oligonucleotide consisting of the bulge and stem/loop structure of HIV TAR which has also been Biotin conjugated. This RNA oligonucleotide was synthesized in house.

A biotinylated HIV RRE RNA oligonucleotide synthesized in house.

Binding buffer: 40 mM Tris-HCl (pH 8.0), 0.01% NP-40, 20% glycerol, 1.5 mM MgCl, 0.01% NaN3, 50 mM KCl.

Streptavidin coated 96 well microtitre plates (Elkay Labsystems).

Protein A/G alkaline phosphatase (Pierce).

Anti tat antiserum (BioDesign).
PNPP substrate (Pierce).
Methods:

To each well of a Streptavidin coated 96 well ELISA plate is added 200 µl of a solution of the 30 base TAR sequence (20 nM) in binding buffer. The plate is incubated at 4° C. for 1 hour. The biotintylated HIV RRE RNA oligonucleotide is bound to selected wells as a negative control RNA. The plate is washed with binding buffer three times and 100 µl of a 100 nM solution of the 39 residue tat peptide in binding buffer is added to each well. Combinatorial libraries or deconvoluted combinatorial libraries are added to selected wells of the plate at initial concentrations of 100 µM. The plate is incubated for 1 hour at room temperature.

The plate is washed with binding buffer three times and blocked with binding buffer +5% FCS. 100 µl of tat antiserum diluted 1:700 in binding buffer is added to the wells of the plate and the plate is incubated for 1.5 hours at 4° C. The plate is washed three times with binding buffer and 150 µL of a solution of protein A/G alkaline phosphatase diluted 1:5000 in binding buffer is added to each well. The plate is incubated for 1.5 hours at 4° C. followed by washing three times with binding buffer. 150 µL of PNPP substrate is added to each well and the plate is incubated for 1 hour at 37° C. The absorbance of each well is read in a multiwell plate reader.

PROCEDURE 5
Antimicrobial Mechanistic Assay
Bacterial DNA Gyrase

DNA gyrase is a bacterial enzyme which can introduce negative supercoils into DNA utilizing the energy derived from ATP hydrolysis. This activity is critical during DNA replication and is a well characterized target for antibiotic inhibition of bacterial growth. In this assay, libraries of compounds are screened for inhibition of DNA gyrase. The assay measures the supercoiling of a relaxed plasmid by DNA gyrase as an electrophoretic shift on an agarose gel. Initially all library pools are screened for inhibitory activity at 30 µM and then a dose response analysis is effected with active subsets. Novobiocin, an antibiotic that binds to the β subunit of DNA gyrase is used as a positive control in the assay. The sensitivity of the DNA gyrase assay was determined by titrating the concentration of the know DNA gyrase inhibitor, Novobiocin, in the supercoiling assay. The $IC_{50}$ was determined to be 8 nM, sufficient to identify the activity of a single active species of comparable activity in a library having 30 µM concentration.

PROCEDURE 6
Use of a combinatorial library for identifying metal chelators and imaging agents This procedure is used to identify compounds of the invention from libraries of compounds constructed to include a ring that contains an ultraviolet chromophore. Further the chemical functional groups attached to the compounds of the invention are selected from metal binders, coordinating groups such as amine, hydroxyl and carbonyl groups, and other groups having lone pairs of electrons, such that the compounds of the invention can form coordination complexes with heavy metals and imaging agents. The procedure is used to identify compounds of the invention useful for chelating and removing heavy metals from industrial broths, waste stream eluents, heavy metal poisoning of farm animals and other sources of contaminating heavy metals, and for use in identifying imaging agent carriers, such as carriers for technetium 99.

An aliquot of a test solution having the desired ion or imaging agent at a known concentration is added to an aliquot of standard solution of the pool under assay. The UV spectrum of this aliquot is measured and is compared to the UV spectrum of a further aliquot of the same solution lacking the test ion or imaging agent. A shift in the extinction coefficient is indicative of binding of the metal ion or imaging ion to a compound in the library pool being assayed.

PROCEDURE 7
Assay of combinatorial library for $PLA_2$ inhibitors

A preferred target for assay of combinatorially generated pools of compounds is the phospholipase $A_2$ family. Phospholipases $A_2$ ($PLA_2$) are a family of enzymes that hydrolyze the sn-2 ester linkage of membrane phospholipids resulting in release of a free fatty acid and a lysophospholipid (Dennis, E. A., The Enzymes, Vol. 16, pp. 307–353, Boyer, P. D., ed., Academic Press, New York, 1983). Elevated levels of type II $PLA_2$ are correlated with a number of human inflammatory diseases. The $PLA_2$-catalyzed reaction is the rate-limiting step in the release of a number of pro-inflammatory mediators. Arachidonic acid, a fatty acid commonly linked at the sn-2 position, serves as a precursor to leukotrienes, prostaglandins, lipoxins and thromboxanes. The lysophospholipid can be a precursor to platelet-activating factor. $PLA_2$ is regulated by pro-inflammatory cytokines and, thus, occupies a central position in the inflammatory cascade (Dennis, ibid.; Glaser et al., *TiPs Reviews* 1992, 14, 92; and Pruzanski et al., *Inflammation* 1992, 16, 451). All mammalian tissues evaluated thus far have exhibited $PLA_2$ activity. At least three different types of $PLA_2$ are found in humans: pancreatic (type I), synovial fluid (type II) and cytosolic. Studies suggest that additional isoenzymes exist. Type I and type II, the secreted forms of $PLA_2$, share strong similarity with phospholipases isolated from the venom of snakes. The $PLA_2$ enzymes are important for normal functions including digestion, cellular membrane remodeling and repair, and in mediation of the inflammatory response. Both cytosolic and type II enzymes are of interest as therapeutic targets. Increased levels of the type II $PLA_2$ are correlated with a variety of inflammatory disorders including rheumatoid arthritis, osteoarthritis, inflammatory bowel disease and septic shock, suggesting that inhibitors of this enzyme would have therapeutic utility. Additional support for a role of $PLA_2$ in promoting the pathophysiology observed in certain chronic inflammatory disorders was the observation that injection of type II $PLA_2$ into the footpad of rats (Vishwanath et al., *Inflammation* 1988, 12, 549) or into the articular space of rabbits (Bomalaski et al., *J. Immunol.* 1991, 146, 3904) produced an inflammatory response. When the protein was denatured before injection, no inflammatory response was produced.

The type II $PLA_2$ enzyme from synovial fluid is a relatively small molecule (about 14 kD) and can be distinguished from type I enzymes (e.g. pancreatic) by the sequence and pattern of its disulfide bonds. Both types of enzymes require calcium for activity. The crystal structures of secreted $PLA_2$ enzymes from venom and pancreatic $PLA_2$, with and without inhibitors, have been reported (Scott et al., *Science* 1990, 250, 1541). Recently, the crystal structure of $PLA_2$ from human synovial fluid has been determined (Wery et al., *Nature* 1991, 352, 79). The structure clarifies the role of calcium and amino acid residues in catalysis. Calcium acts as a Lewis acid to activate the scissile ester carbonyl bond of 1,2-diacylglycerophospholipids and binds to the lipid, and a His-Asp side chain diad acts as a general base catalyst to activate a water molecule nucleophile. This is consistent with the absence of any acyl enzyme intermediates, and is also comparable to the catalytic mechanism of serine proteases. The catalytic residues and the calcium ion are at the end of a deep cleft (ca. 14 Å) in the enzyme. The walls of this cleft contact the hydrocarbon portion of the phospholipid and are composed of hydrophobic and aromatic residues. The positively-charged amino-terminal helix is situated above the opening of the hydrophobic cleft. Several lines of evidence suggest that the N-terminal portion is the interfacial binding site (Achari et al., *Cold Spring Harbor Symp. Quant. Biol.* 1987, 52, 441; Cho et al., *J. Biol. Chem.* 1988, 263, 11237; Yang et al., *Biochem. J.* 1989, 262, 855; and Noel et al., *J. Am. Chem. Soc.* 1990, 112, 3704).

Much work has been reported in recent years on the study of the mechanism and properties of $PLA_2$-catalyzed hydrolysis of phospholipids. In in vitro assays, $PLA_2$ displays a lag phase during which the enzyme adsorbs to the substrate bilayer and a process called interfacial activation occurs. This activation may involve desolvation of the enzyme/lipid interface or a change in the physical state of the lipid around the cleft opening. Evidence favoring this hypothesis comes from studies revealing that rapid changes in $PLA_2$ activity occur concurrently with changes in the fluorescence of a membrane probe (Burack et al., *Biochemistry* 1993, 32, 583). This suggests that lipid rearrangement is occurring during the interfacial activation process. $PLA_2$ activity is maximal around the melting temperature of the lipid, where regions of gel and liquid-crystalline lipid coexist. This is also consistent with the sensitivity of $PLA_2$ activity to temperature and to the composition of the substrate, both of which can lead to structurally distinct lipid arrangements separated by a boundary region. Fluorescence microscopy was used to simultaneously identify the physical state of the lipid and the position of the enzyme during catalysis (Grainger et al., *FEBS Lett.* 1989, 252, 73). These studies clearly show that $PLA_2$ binds exclusively at the boundary region between liquid and solid phase lipid. While the hydrolysis of the secondary ester bond of 1,2-diacylglycerophospholipids catalyzed by the enzyme is relatively simple, the mechanistic and kinetic picture is clouded by the complexity of the enzyme-substrate interaction. A remarkable characteristic of $PLA_2$ is that maximal catalytic activity is observed on substrate that is aggregated (i.e. phospholipid above its critical micelle concentration), while low levels of activity are observed on monomeric substrate. As a result, competitive inhibitors of $PLA_2$ either have a high affinity for the active site of the enzyme before it binds to the substrate bilayer or partition into the membrane and compete for the active site with the phospholipid substrate. Although a number of inhibitors appear to show promising inhibition of $PLA_2$ in biochemical assays (Yuan et al., *J. Am. Chem. Soc.* 1987, 109, 8071; Lombardo et al., *J. Biol. Chem.* 1985, 260, 7234; Washburn et al., *J. Biol. Chem.* 1991, 266, 5042; Campbell et al., *J. Chem. Soc., Chem. Commun.* 1988, 1560; and Davidson et al., *Biochem. Biophys. Res. Commun.* 1986, 137, 587), reports describing in vivo activity are limited (Miyake et al., *J. Pharmacol. Exp. Ther.* 1992, 263, 1302).

In one preferred embodiment, compounds of the invention are selected for their potential to interact with, and preferably inhibit, the enzyme $PLA_2$. Thus, compounds of the invention can be used for topical and/or systemic treatment of inflammatory diseases including atopic dermatitis and inflammatory bowel disease. In selecting the functional groups, advantage can be taken of $PLA_2$'s preference for anionic vesicles over zwitterionic vesicles. Preferred compounds of the invention for assay for $PLA_2$ include those having aromatic diversity groups to facilitate binding to the cleft of the $PLA_2$ enzyme (Oinuma et al., *J. Med. Chem.* 1991, 34, 2260; Marki et al., *Agents Actions* 1993, 38, 202; and Tanaka et al., *J. Antibiotics* 1992, 45, 1071). Benzyl and 4-hexylbenzyl groups are preferred aromatic diversity groups. $PLA_2$-directed compounds of the invention can further include hydrophobic functional groups such as tetraethylene glycol groups. Since the $PLA_2$ enzyme has a hydrophobic channel, hydrophobicity is believed to be an important property of inhibitors of the enzyme.

After each round of synthesis as described in the above examples, the resulting libraries or pools of compounds are screened for inhibition of human type II $PLA_2$ enzymatic activity. The assay is effected at the conclusion of each round of synthesis to identify the wining pool from that round of synthesis. Concurrently, the libraries additionally can be screened in other in vitro assays to determine further mechanisms of inhibition.

The pools of the libraries are screened for inhibition of $PLA_2$ in the assay using *E. coli* labeled with $^3$H-oleic acid (Franson et al., *J. Lipid Res.* 1974, 15, 380; and Davidson et al., *J. Biol. Chem.* 1987, 262, 1698) as the substrate. Type II $PLA_2$ (originally isolated from synovial fluid), expressed in a baculovirus system and partially purified, serves as a source of the enzyme. A series of dilutions of each of the library pools is done in water: 10 µl of each pool is incubated for 5 minutes at room temperature with a mixture of 10 µl $PLA_2$, 20 µl 5X $PLA_2$ Buffer (500 mM Tris 7.0–7.5, 5 mM $CaCl_2$), and 50 µl water. Samples of each pool are run in duplicate. At this point, 10 µl of $^3$H *E. coli* cells is added. This mixture is incubated at 37° C. for 15 minutes. The enzymatic reaction is stopped with the addition of 50 µL 2M HCl and 50 µL fatty-acid-free BSA (20 mg/mL PBS), vortexed for 5 seconds, and centrifuged at high speed for 5 minutes. 165 µL of each supernate is then put into a scintillation vial containing 6 ml of scintillant (ScintiVerse) and cpms are measured in a Beckman Liquid Scintillation Counter. As a control, a reaction without the combinatorial pool is run alongside the other reactions as well as a baseline reaction containing no compounds of the invention as well as no $PLA_2$ enzyme. CPMs are corrected for by subtracting the baseline from each reaction data point.

Confirmation of the "winners" is made to confirm that a compound of the invention binds to enzyme rather than substrate and that the inhibition by a compound of the invention that is selected is specific for type II $PLA_2$. An assay using $^{14}$C-phosphatidyl ethanolamine ($^{14}$C-PE) as substrate, rather than *E. coli* membrane, is used to insure enzyme rather than substrate specificity. Micelles of $^{14}$C-PE and deoxycholate are incubated with the enzyme and a compound of the invention. $^{14}$C-labeled arachidonic acid released as a result of $PLA_2$-catalyzed hydrolysis is separated from substrate by thin layer chromatography and the radioactive product is quantitated. The "winner" is compared to phosphatidyl ethanolamine, the preferred substrate of human type II $PLA_2$, to confirm its activity. $PLA_2$ from other sources (snake venom, pancreatic, bee venom) and phospholipase C, phospholipase D and lysophospholipase can be used to further confirm that the inhibition is specific for human type II $PLA_2$.

PROCEDURE 8

Probes for the detection of specific proteins and mRNA in biological samples

For the reliable, rapid, simultaneous quantification of multiple varieties of proteins or mRNA in a biological sample without the need to purify the protein or mRNA from other cellular components, a protein or mRNA of interest from a suitable biological sample, i.e., a blood borne virus, a bacterial pathogen product in stool, urine and other like biological samples, is identified using standard microbiological techniques. A probe comprising a compound of a combinatorial library of the invention is identified by a combinatorial search as noted in the above examples. Preferred for the protein probe are compounds synthesized to include chemical functional groups that act as hydrogen bond donors and acceptors, sulfhydryl groups, hydrophobic lipophilic moieties capable of hydrophobic interactions groups and groups capable of ionic interactions. The probe is immobilized on insoluble CPG solid support utilizing the procedure of Pon, R. T., Protocols for Oligonucleotides and Analogs, Agrawal, S., Ed., Humana Press, Totowa, N.J., 1993, p 465–496. A known aliquot of the biological sample under investigation is incubated with the insoluble CPG support having the probe thereon for a time sufficient to hybridize the protein or mRNA to the probe and thus form a linkage via the probe to the solid support. This immobilizes the protein or mRNA present in the sample to the CPG support. Other non-immobilized materials and components are then washed off the CPG with a wash media suitable for use with the biological sample. The mRNA on the support is labeled with ethidium bromide, biotin or a commercial radionucleotide and the amount of label immobilized on the CPG support is measured to indicate the amount of mRNA present in the biological sample. In a similar assay a protein is also labeled and quantified.

PROCEDURE 9

Leukotriene $B_4$ assay

Leukotriene $B_4$ ($LTB_4$) has been implicated in a variety of human inflammatory diseases, and its pharmacological effects are mediated via its interaction with specific surface cell receptors. Library subsets are screened for competitive inhibition of radiolabeled $LTB_4$ binding to a receptor preparation.

A Nenquest™ Drug Discovery System Kit (NEN Research Products, Boston, Mass.) is used to select an inhibitor of the interaction of Leukotriene $B_4$ ($LTB_4$) with receptors on a preparation of guinea pig spleen membrane. [$^3$H] Leukotriene $B_4$ reagent is prepared by adding 5 mL of ligand diluent (phosphate buffer containing NaCl, $MgCl_2$, EDTA and Bacitracin, pH 7.2) to 0.25 mL of the radioligand. The receptor preparation is made by thawing the concentrate, adding 35 mL of ligand diluent and swirling gently in order to re-suspend the receptor homogeneously. Reagents are kept on ice during the course of the experiment, and the remaining portions are stored at −20° C.

Library subsets prepared as per general procedure of examples above are diluted to 5 μM, 50 μM and 500 μM in phosphate buffer (1× PBS, 0.1% azide and 0.1% BSA, pH 7.2), yielding final test concentrations of 0.5 μM, 5 μM and 50 μM, respectively. Samples are assayed in duplicate. [$^3$H] $LTB_4$ (25 μL) is added to 25 μL of either appropriately diluted standard (unlabeled $LTB_4$) or library subset. The receptor suspension (0.2 mL) is added to each tube. Samples are incubated at 4° C. for 2 hours. Controls include [$^3$H] $LTB_4$ without receptor suspension (total count vials), and sample of ligand and receptor without library molecules (standard).

After the incubation period, the samples are filtered through GF/B paper that had been previously rinsed with cold saline. The contents of each tube are aspirated onto the filter paper to remove unbound ligand from the membrane preparation, and the tubes washed (2×4 mL) with cold saline. The filter paper is removed from the filtration unit and the filter disks are placed in appropriate vials for scintillation counting. Fluor is added, and the vials shaken and allowed to stand at room temperature for 2 to 3 hours prior to counting. The counts/minute (cpm) obtained for each sample are subtracted from those obtained from the total counts to determine the net cpm for each sample. The degree of inhibition of binding for each library subset is determined relative to the standard (sample of ligand and receptor without library molecules).

Those skilled in the art will appreciate that numerous changes and modifications may be made to the preferred embodiments of the present invention and that such changes and modifications may be made without departing from the spirit of the invention. It is therefore intended that the appended claims cover all such equivalent variations as fall within the true spirit and scope of the invention.

What is claimed is:

1. A composition comprising at least three different compounds, each of said compounds having the formula:

wherein each p is independently 0, 1 or 2;

each x and y are independently 1, 2 or 3;

each $Q_1$ is independently —N($R_{15}$)—, —O— or —S—;

each $R_2$ is hydrogen, $C_1$–$C_6$ alkyl, $C_6$–$C_{15}$ aryl, $C_7$–$C_{20}$ alkaryl, or a moiety of the formula —($CH_2$)$_m$—$R_3$—$R_4$, where:

each m is 0 or 1;

each $R_3$ is —$CH_2$—, —C(=O)— or —C(=S)—; and each $R_4$ is —O—$R_5$, $C_1$–$C_6$ alkyl, $C_6$–$C_{15}$ aryl or where $R_5$ is hydrogen, $C_1$–$C_6$ alkyl, $C_6$–$C_{15}$ aryl, $C_3$–$C_{12}$ cycloalkyl, or $C_7$–$C_{20}$ alkaryl;

each $R_{11}$ is independently hydrogen, $C_1$–$C_6$ alkyl, $C_7$–$C_{20}$ alkaryl, $C_6$–$C_{20}$ aryl, or $C_3$–$C_{20}$ cycloalkyl;

each $R_{12}$ is independently —$CH_2$— or —C(=O)—; and each $R_{15}$ is independently hydrogen or $C_1$–$C_6$ alkyl.

2. The composition of claim 1 wherein at least one p is independently 0 or 1; and x and y are independently 2 or 3.

3. The composition of claim 1 wherein at least one p is 1; and x and y are 2.

4. The composition of claim 1 wherein at least one $Q_1$ is —N($R_{15}$)—.

5. The composition of claim 1 wherein at least one $R_{11}$ is $C_1$–$C_6$ alkyl, $C_7$–$C_{20}$ alkaryl, $C_6$–$C_{20}$ aryl or $C_3$–$C_{20}$ cycloalkyl.

6. The composition of claim 5 wherein at least one $R_{11}$ is $C_7$–$C_{20}$ alkaryl, $C_6$–$C_{20}$ aryl or $C_3$–$C_{20}$ cycloalkyl.

7. The composition of claim 6 wherein at least one $R_{11}$ is $C_6$–$C_{20}$ aryl or $C_3$–$C_{20}$ cycloalkyl.

8. The composition of claim 7 wherein at least one $R_{11}$ is selected from the group consisting of substituted or unsubstituted phenyl, cyclopropyl, cyclobutyl, cyclopentyl, cyclohexyl, cycloheptyl, cyclooctyl, cyclononyl, cyclodecyl and cyclododecyl.

9. The composition of claim 8 wherein at least one $R_{11}$ is p-methoxyphenyl.

10. The composition of claim 8 wherein at least one $R_{11}$ is cycloheptyl.

11. The composition of claim 8 wherein at least one $R_{11}$ is cycloheptyl.

12. The composition of claim 1 wherein $R_{15}$ is hydrogen.

13. The composition of claim 1 wherein at least one $R_{12}$ is —C(=O)—.

14. The composition of claim 1 wherein at least one $R_{12}$ is —$CH_2$—.

15. The composition of claim 1 wherein at least one $R_2$ is $C_6$–$C_{15}$ aryl.

16. The composition of claim 1 wherein at least one $R_2$ is phenyl, m-trifluoromethylphenyl or o-halophenyl.

17. The composition of claim 1 wherein at least one $R_2$ is m-trifluoromethylphenyl or o-halophenyl.

18. The composition of claim 1 wherein at least one $R_2$ is $C_7$–$C_{20}$ alkaryl.

19. The composition of claim 1 wherein at least one $R_2$ is benzyl, m-methylbenzyl, m-nitrobenzyl, m-fluorobenzyl, m-cyanobenzyl, m-trifluoromethylbenzyl or m-methylcarboxylbenzyl.

20. The composition of claim 1 wherein at least one $R_2$ is a moiety of the formula —$(CH_2)_m$—$R_3$—$R_4$ where:

m is 0 or 1;

$R_3$ is —$CH_2$—, —C(=O)— or —C(=S)—; and $R_4$ is —O—$R_5$, $C_1$–$C_6$ alkyl, $C_6$–$C_{15}$ aryl.

21. The composition of claim 1 comprising at least six of said compounds.

22. The composition of claim 1 comprising at least twenty of said compounds.

23. The composition of claim 1 exhibiting antibacterial activity.

24. The composition of claim 1 in a pharmaceutically acceptable carrier or diluent.

* * * * *